United States Patent
Hammer et al.

(10) Patent No.: US 8,444,268 B2
(45) Date of Patent: *May 21, 2013

(54) STABILIZED RETINAL IMAGING WITH ADAPTIVE OPTICS

(75) Inventors: Daniel X. Hammer, Bedford, NH (US); R. Daniel Ferguson, Melrose, MA (US); Nicusor V. Iftimia, Chelmsford, MA (US); Teoman E. Ustun, Malden, MA (US)

(73) Assignee: Physical Sciences, Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/009,457

(22) Filed: Jan. 19, 2011

(65) Prior Publication Data

US 2011/0152845 A1    Jun. 23, 2011

Related U.S. Application Data

(63) Continuation of application No. 12/817,789, filed on Jun. 17, 2010, now Pat. No. 7,896,496, which is a continuation of application No. 11/789,800, filed on Apr. 24, 2007, now Pat. No. 7,758,189.

(60) Provisional application No. 60/794,359, filed on Apr. 24, 2006.

(51) Int. Cl.
*A61B 3/14* (2006.01)

(52) U.S. Cl.
USPC .......................................................... 351/206

(58) Field of Classification Search
USPC .......................................................... 351/206
See application file for complete search history.

(56) References Cited

U.S. PATENT DOCUMENTS

| 4,264,152 A | 4/1981 | Crane |
| 4,443,075 A | 4/1984 | Crane |
| 4,561,436 A | 12/1985 | Munnerlyn |
| 4,569,354 A | 2/1986 | Shapiro et al. |

(Continued)

FOREIGN PATENT DOCUMENTS

| EP | 0 307 185 | 3/1989 |
| EP | 0 770 370 | 5/1997 |

(Continued)

OTHER PUBLICATIONS

Alt et al., "Selective Targeting of the Retinal Pigment Epithelium Using an Acousto-Optic Laser Scanner," *Journal of Biomedical Optics*, vol. 10(6) (2005) pp. 064014-1-064014-11. (11 pgs.).

(Continued)

*Primary Examiner* — James Jones
(74) *Attorney, Agent, or Firm* — Proskauer Rose LLP

(57) ABSTRACT

A system provides an optical image of an object. A first module tracks a reference feature of the object. A second module includes a source for an imaging beam, a scanning device to move the imaging beam along a portion of the object and a detection device receives a signal associated with an image of the portion of the object. The first module controls the position of the imaging beam relative to the reference feature to correct for the motion of the object. A third module detects a distortion of the object and compensates for the distortion.

17 Claims, 11 Drawing Sheets

U.S. PATENT DOCUMENTS

| | | | |
|---|---|---|---|
| 4,764,005 | A | 8/1988 | Webb et al. |
| 4,765,730 | A | 8/1988 | Webb |
| 4,768,873 | A | 9/1988 | Webb |
| 4,768,874 | A | 9/1988 | Webb et al. |
| 4,781,453 | A | 11/1988 | Kobayashi |
| 4,856,891 | A | 8/1989 | Pflibsen et al. |
| 4,881,808 | A | 11/1989 | Bille et al. |
| 4,883,061 | A | 11/1989 | Zeimer |
| 4,886,351 | A | 12/1989 | Sabban et al. |
| 4,924,507 | A | 5/1990 | Chao et al. |
| 4,931,053 | A | 6/1990 | L'Esperance, Jr. |
| 4,964,717 | A | 10/1990 | Koester |
| 5,029,220 | A | 7/1991 | Juday |
| 5,094,523 | A | 3/1992 | Reznichenko et al. |
| 5,098,426 | A | 3/1992 | Sklar et al. |
| 5,106,184 | A | 4/1992 | Milbocker |
| 5,122,135 | A | 6/1992 | Dürr et al. |
| 5,129,400 | A | 7/1992 | Makino et al. |
| 5,243,368 | A | 9/1993 | Ito et al. |
| 5,252,999 | A | 10/1993 | Sukigara et al. |
| 5,309,187 | A | 5/1994 | Crossman et al. |
| 5,347,329 | A | 9/1994 | Ota |
| 5,353,073 | A | 10/1994 | Kobayashi |
| 5,360,010 | A | 11/1994 | Applegate |
| 5,360,424 | A | 11/1994 | Klopotek |
| 5,425,729 | A | 6/1995 | Ishida et al. |
| 5,430,509 | A | 7/1995 | Kobayashi |
| 5,437,274 | A | 8/1995 | Khoobehi et al. |
| 5,480,396 | A | 1/1996 | Simon et al. |
| 5,526,189 | A | 6/1996 | Heacock |
| 5,673,097 | A | 9/1997 | Heacock |
| 5,767,941 | A | 6/1998 | Ferguson |
| 5,777,719 | A | 7/1998 | Williams et al. |
| 5,778,016 | A | 7/1998 | Sucha et al. |
| 5,784,148 | A | 7/1998 | Heacock |
| 5,861,938 | A | 1/1999 | Heacock |
| 5,943,115 | A | 8/1999 | Ferguson |
| 5,949,520 | A | 9/1999 | Heacock |
| 5,976,502 | A | 11/1999 | Khoobehi et al. |
| 6,027,216 | A | 2/2000 | Guyton et al. |
| 6,099,127 | A | 8/2000 | Manivannan et al. |
| 6,186,628 | B1 | 2/2001 | Van de Velde |
| 6,199,986 | B1 | 3/2001 | Williams et al. |
| 6,267,477 | B1 | 7/2001 | Karpol et al. |
| 6,299,311 | B1 | 10/2001 | Williams et al. |
| 6,331,059 | B1 | 12/2001 | Kudryashov et al. |
| 6,379,006 | B1 | 4/2002 | Eikelboom et al. |
| 6,471,691 | B1 | 10/2002 | Kobayashi et al. |
| 6,582,079 | B2 | 6/2003 | Levine |
| 6,758,564 | B2 | 7/2004 | Ferguson |
| 6,890,076 | B2 | 5/2005 | Roorda |
| 7,118,216 | B2 | 10/2006 | Roorda |
| 7,284,862 | B1 * | 10/2007 | Lai et al. .................. 351/209 |
| 2005/0012899 | A1 | 1/2005 | Ferguson |
| 2005/0254008 | A1 | 11/2005 | Ferguson et al. |

FOREIGN PATENT DOCUMENTS

| | | |
|---|---|---|
| WO | WO 90/09141 | 8/1990 |
| WO | WO 93/08877 | 5/1993 |
| WO | WO 95/28989 | 11/1995 |
| WO | WO 97/40405 | 10/1997 |
| WO | WO 03/105678 | 12/2003 |
| WO | WO 03/105679 | 12/2003 |

OTHER PUBLICATIONS

Hammer et al., "High Resolution Retinal Imaging With a Compact Adaptive Optics Spectral Domain Optical Coherance Tomography System," *Proceedings of SPIE*, vol. 6426 (2007) pp. 64261Q-1-64261Q-10. (10 pgs.).

Kobayashi et al., "Confocal Scanning Laser Ophthalmoscope With a Slit Aperture," *Measurement Science and Technology*, vol. 2 (1991) pp. 287-292. (6 pgs.).

Hammer et al., "Compact Scanning Laser Ophthalmoscope With High-Speed Retinal Tracker," *Applied Optics*, vol. 42, No. 22 (2003) pp. 4621-4632.

Heacock et al., "Imaging of the Choroid With the Scanning Slit Laser Ophthalmosocpe (SSLO)," *The Society for Photo-Optical Instrumentation Engineers (SPIE)*, vol. 3591 pp. 456-464. (9 pgs.)

Hammer et al, "Precision Targeting With a Tracking Adaptive Optics Scanning Laser Ophthalmoscope," *Presented at SPIE BIOS 2006 Advaced Biomedical and Clinical and Diagnostic Systems IV* (San Jose, CA) (Jan. 21-26, 2006), [online],.[retrieved on Jul. 31, 2007]. Retrieved from the Internet <URL: http://www.psicorp.com/publications/PDF/sr-1256.pdf> (11 pgs.)

Hammer et al., "Adaptive Optics Scanning Laser Ophthalmoscope for Stabilized Retinal Imaging," *Optics Express*, vol. 14, No. 8 (2006) pp. 3354-3367.

Bigelow et al., "Compact Multimodal Adaptive-Optics Spectral-Domain Optical Coherence Tomography Instrument for Retinal Imaging," *Journal of the Optical Society of America A*, vol. 24, No. 5 (May 2007) pp. 1327-1336. (10 pgs.).

Dreher et al., "Active Optical Depth Resolution Improvement of the Laser Tomographic Scanner," *Applied Optics*, vol. 28, No. 4 (1989) pp. 804-808. (5 pgs.).

Iftimia, et al. "Hybrid Retinal Imager Using Line-Scanning Laser Ophthalmoscopy and Spectral Domain Optical Coherence Tomography," *Optics Express*, vol. 14, No. 26 (2006) pp. 12909-12914. (12 pgs.).

Ferguson, et al "Tracking Adaptive Optics Scanning Laser Ophthalmoscope," *Proceedings of SPIE*, vol. 6138 (2006) pp. 613810-1-613810-9. (9 pgs.)

Hammer, et al. "Hybrid LSLO/SDOCT retinal imager," [online], [retrieved on Jul. 31, 2007]. Retrieved from the Internet <URL:http://www.psicorp.com/publications/PDF/sr-1287.pdf> (9 pgs.).

Department of Defense Handbook, "Laser Safety on Ranges and in Other Outdoor Areas," MIL-HDBK-828A, Appendix A: "Summary of Laser Safety Information for Fire Control Laser Systems." (Dec. 31, 1996) (136 pgs.).

Johnson et al., "Laser Eye Injuries Among US Military Personnel," *Proceedings of SPIE*, vol. 4953 (2003) pp. 51-60. (10 pgs.).

Sasahara et al., "Optical Coherence Tomographic Observations Before and After Macular Hole Formation Secondary to Laser Injury," *American Journal of Ophthalmology*, vol. 136, No. 6 (2003) pp. 1167-1170. (4 pgs.).

Sakaguchi et al., "Amsler Grid Examination and Optical Coherence Tomography of a Macular Hole Caused by Accidental Nd:YAG Laser Injury," *American Journal of Ophthalmology*, vol. 130, No. 3 (2000) pp. 355-356. (2 pgs.).

Roach et al., "Retinal Response of *Macaca mulatta* to Picosecond Laser Pulses of Varying Energy and Spot Size," *Journal Biomedical Optics*, in press, vol. 9, No. 6 (2004) pp. 1288-1296. (9 pgs.).

Webb, et al., "Confocal Scanning Laser Ophthalmoscope," *Applied Optics*, vol. 26, No. 8 (1987) pp. 1492-1499. (8 pgs.).

Ferguson et al., "A Line-Scanning Laser Ophthalmoscope (LSLO)," *Investigative Ophthalmology & Visual Science*, (2003). (2 pgs.).

Hammer et al., "Hand-Held Digital Line-Scanning Laser Ophthalmoscope (LSLO)," *Proceedings of SPIE*, vol. 5314 (2004) pp. 161-169. (9 pgs.)

Huang et al., "Optical Coherence Tomography," *Science*, vol. 254 (1991) pp. 1178-1181. (4 pgs.).

Cense et al., "In Vivo Depth-Resolved Birefringence Measurements of the Human Retinal Nerve Fiber Layer by Polarization-Sensitive Optical Coherence Tomography," *Optics Letters*, vol. 27, No. 18 (2002) pp. 1610-1612. (3 pgs.).

Park et al., "Real-Time Multi-Functional Optical Coherence Tomography," *Optics Express*, vol. 11, No. 7 (2003) pp. 782-793. (12 pgs.).

Fercher et al., "Measurement of Intraocular Distances by Backscattering Spectral Interferometry," *Optics Communications*, vol. 117 (1995) pp. 43-48. (6 pgs.).

Hausler et al., "'Coherence Radar' and 'Spectral Radar'—New Tools for Dermatological Diagnosis," *Journal of Biomedical Optics*, vol. 3, No. 1, (1998) pp. 21-31. (11 pgs.).

Fercher et al., Optical Coherence Tomography—Principles and Applications, *Institute of Physics Publishing Reports on Progress in Physics*, vol. 66 (2003) pp. 239-303. (65 pgs.).

"American National Standard for Safe Use of Lasers" *Laser Institute of America*, (2000). (185 pgs.).

Yun et al., "High-Speed Optical Frequency-Domain Imaging," *Optics Express*, vol. 11, No. 22 (2003) pp. 2953-2963. (9 pgs.).

Drexler Wet et al., "Enhanced Visualization of Macular Pathology With the Use of Ultrahigh-Resolution Optical Coherence Tomography," *Archives of Ophthalmology*, vol. 121 (2003) pp. 695-706. (12 pgs.).

Wojtkowski et al., "In Vivo Human Retinal Imaging by Fourier Domain Optical Coherence Tomography," *Journal of Biomedical Optics*, vol. 7, No. 3 (2002) pp. 457-463. (7 pgs.).

Wojtkowski et al., "Real-Time in Vivo Imaging by High-Speed Spectral Optical Coherence Tomography," *Optics Letters*, vol. 28, No. 19 (2003) pp. 1745-1747. (3 pgs).

Yun et al., "High-Speed Spectral-Domain Optical Coherence Tomography at 1.3 μm Wavelength," *Optics Express*, vol. 11, No. 26, (2003) pp. 3598-3604. (7 pgs.).

Leitgeb et al., "Performance of Fourier Domain vs. Time Domain Optical Coherence Tomography," *Optics Express*, vol. 11, No. 8 (2003) pp. 889-894 (6 pgs.).

de Boer et al., "Improved Signal-to Noise Ratio Spectral-Domain Compared with Time-Domain Optical Coherence Tomography," *Optics Letters*, vol. 28, No. 21 (2003) pp. 2067-2069. (3 pgs.).

White et al., "In Vivo Dynamic Human Retinal Blood Flow Imaging Using Ultra-High-Speed Domain Optical Doppler Tomography," *Optics Express*, vol. 11, No. 25 (2003) pp. 3490-3497. (8 pgs.).

Nassif et al., "In Vivo High-Resolution Video-Rate Spectral-Domain Optical Coherence Tomography of the Human Retina and Optic Nerve," *Optics Express*, vol. 12, No. 3 (2004) pp. 367-376. (10 pgs.).

Hammer, et al., "Technological Advances Improve Retinal Diagnostics," *Biophotonics International*, vol. 10, No. 9 (2003) p. 20. (2 pgs.).

Hammer et al., "Image Stabilization for Scanning Laser Ophthalmoscopy," *Optics Express*, vol. 10, No. 26 (2002) pp. 1542-1549. (8 pgs.).

Hammer et al., "Tracking Scanning Laser Ophthalmoscope (TSLO)," *Proceedings of SPIE*, vol. 4951 (2003) pp. 208-217. (10 pgs.).

Hammer et al., "Active Retinal Tracker for Clinical Optical Coherence Tomography Systems," *Journal of Biomedical Optics*, in press. vol. 10(2) (2005) pp. 024038-1-024038-11. (11 pgs.).

Ferguson et al., "Tracking Optical Coherence Tomography," *Optics Letters*, vol. 29, No. 18 (2004) pp. 2139-2141. (3 pgs.).

Hammer et al., "Advanced Scanning Methods With Tracking Optical Coherence Tomography," *Optics Express*, vol. 13, No. 20 (2005) pp. 7937-7947. (11 pgs.)

Ferguson et al., "Wide-Field Retinal Hemodynamic Imaging With the Tracking Scanning Laser Ophthalmoscope," *Optics Express*, vol. 12, No. 21 (2004) pp. 5198-5208. (11 pgs.).

Ishikawa et al., "Retinal Nerve Fiber Layer Assessment Using Optical Coherence Tomography With Active Optic Nerve Head Tracking," *Investigative Ophthalmology & Visual Science*, vol. 47, No. 3 (2006) pp. 964-967. (4 pgs.).

Liang et al., "Supernormal Vision and High-Resolution Retinal Imaging Through Adaptive Optics," *Journal of the Optical Society of America A*, vol. 14, No. 11 (1997) pp. 2884-2892. (9 pgs.)

Roorda et al., "Adaptive Optics Scanning Laser Ophthalmoscopy," *Optics Express*, vol. 10, No. 9 (2002) pp. 405-412. (8 pgs.).

Hammer et al., "Line-Scanning Laser Ophthalmoscope," *Journal of Biomedical Optics*, vol. 11(4) (2006) pp. 041126-1-041126-10. (10 pgs.).

Thibos et al., "Standards for Reporting the Optical Aberrations of Eyes," *Journal of Refractive Surgery*, vol. 18 (2002) pp. S652-S660. (9 pgs.).

Curcio et al., "Packing Geometry of Human Cone Photoreceptors: Variations With Eccentricity and Evidence for Local Anisotropy," *Visual Neuroscience*, vol. 9 (1992) pp. 169-180. (12 pgs.).

Vogel et al., "Retinal Motion Estimation in Adaptive Optics Scanning Laser Ophthalmoscopy," *Optics Express*, vol. 14, No. 2 (2006) pp. 487-497. (11 pgs.).

International Search Report for International Application No. PCT/US2007/10107, Date of Mailing Dec. 10, 2007 (8 pages total).

\* cited by examiner

STABILIZED RETINAL IMAGING WITH ADAPTIVE OPTICS

CROSS-REFERENCE TO RELATED APPLICATION

This application is a continuation of U.S. patent application Ser. No. 12/817,789 filed Jun. 17, 2010, which is a continuation of U.S. patent application Ser. No. 11/789,800 filed Apr. 24, 2007, now U.S. Pat. No. 7,758,189, which claims the benefit of and priority to U.S. provisional patent application No. 60/794,359 filed Apr. 24, 2006, all of which are owned by the assignee of the instant application and the disclosures of which are incorporated herein by reference in their entireties.

STATEMENT OF GOVERNMENT INTEREST

This invention was made with government support under Contract Nos. R21EB003111 and R01EY14375 awarded by the National Institute of Health and Contract No. FA8650-05-C-6552 awarded by the United States Air Force. The government may have certain rights in the invention.

FIELD OF THE INVENTION

The invention relates generally to a method and apparatus for optical imaging including a module to correct for movement of an object and a module to correct for distortions of an object.

BACKGROUND OF THE INVENTION

Adaptive optics (AO) instruments are used in ophthalmology to sense and correct ocular aberrations and provide high transverse resolution imaging. AO systems couple a wave-front sensor (e.g., Hartmann-Shack (HS-WS)) and a wave-front compensator (e.g., deformable mirror, DM) to actively correct distortions that can be caused mainly by the tear film, cornea, and lens. For adaptive optics systems, the high magnification necessary to resolve small structures such as photoreceptors are concomitant with smaller fields of view of about 1-2 deg (300-600 µm). Eye motion for even the best fixators can be up to 0.5 deg and slew targets of interest out of the field of view lowering the duty factor of useable images from a given session. AO systems also suffer from the requirement that reasonable pupil centration be maintained during wave-front sensing. Thus, translational head motion and anterior segment tracking are also important to these systems. Clinical utility for AO instruments may necessitate alternate auxiliary wide-field imaging to place the smaller fields at precise locations on the retina. This is analogous to the general requirement that clinical OCT systems, which generate primarily cross-sectional views, also include a secondary imaging system to display a more traditional en-face fundus view. In the case of AO systems, there is often uncertainty about the location of the smaller field relative to global landmarks. Retinal tracking, dual imaging, and a well-designed operator interface can aid in the development of advanced clinical functionality and further progress in vision research.

SUMMARY OF THE INVENTION

The invention, in various embodiments, features a system to direct aberration-corrected laser beams to the retina for diagnosis (e.g., including imaging and stimulation), therapy, and vision studies. The system enables early detection and precision laser treatment for retinal diseases such as age-related macular degeneration and diabetic retinopathy. Moreover, the platform can be used in studies to increase our understanding of the mechanisms of vision by stimulation of individual ganglion cells, photoreceptors, and other cells important for light transduction. In some embodiments, the system combines components for adaptive optics, retinal tracking, auxiliary (therapeutic or stimulus) beam delivery, and imaging, which can include wide-field line scanning laser ophthalmoscopy, high-resolution confocal scanning laser ophthalmoscopy, any variety (time-domain, spectrometer or swept-source-based Fourier domain) of optical coherence tomography, or any combination of these techniques. A therapeutic laser can be delivered using ultra-short (<1 µs) pulses for microsurgery. The adaptive optics can provide precise images of targets to confine lateral and axial damage. An ultra-short laser pulse can further confine the damage.

In some embodiments, the system is a retinal imaging instrument that integrates adaptive optics, scanning laser ophthalmoscopy, and retinal tracking components. In some embodiments, the system is a retinal imaging instrument that integrates adaptive optics, Fourier domain optical coherence tomography, and retinal tracking components. The system can use a Hartmann-Shack wave-front sensor (HSWS) and MEMS-based deformable mirror (DM) for AO-correction of high-resolution, confocal SLO or high-speed, high axial resolution OCT images. In some embodiments, the system includes a wide-field line scanning laser ophthalmoscope for orientation of the high magnification SLO raster or OCT scan. The AO system can be used to correct ocular aberrations to less than about 0.1 µm RMS wave-front error. An active retinal tracker with a real-time digital signal processing board can sense and correct eye motion with a bandwidth exceeding about 1 kHz. Utilizing a preferred embodiment of the retinal imaging system can generate a tracking accuracy down to about 6 µm RMS for some subjects, while the typical performance of the retinal imaging system had a tracking accuracy of about 10-15 µm RMS. The system can be used by clinicians and researchers for vision studies and the early detection and treatment of retinal diseases.

In one aspect, there is an apparatus that includes a first module to track a reference feature of a retina of an eye, a second module to generate an image of the retina of an eye, and a third module to detect and correct for optical distortions. The second module includes a source for an imaging beam, a scanning device to move the imaging beam along a portion of the retina of the eye and a first detection device to receive a signal associated with an image of the portion of the retina scanned. The first module controls the position of the imaging beam relative to the reference feature to correct for motion of the eye. The third module includes a wavefront sensor to detect an optical distortion and a wavefront compensator to correct for the optical distortion in the imaging beam scanned on the retina of the eye.

In another aspect, there is a method for imaging a retina of an eye. The method includes tracking a reference feature of the retina of the eye and scanning an imaging beam along a portion of the retina. The method controls the position of the imaging beam relative to the reference feature to correct for motion of the eye. A signal associated with an image of the portion of the retina scanned is detected. The method compensates for an optical distortion of the image of the retina by correcting the imaging beam scanned on the retina.

In still another aspect, there is a method for imaging a retina of an eye. The method includes tracking a reference feature of the retina of the eye and scanning an imaging beam along a portion of the retina using a sinusoidal scan. The method controls the position of the imaging beam relative to the reference feature to correct for motion of the eye. A signal associated with an image of the portion of the retina scanned is detected. The method compensates for an optical distortion of the image of the retina by correcting the imaging beam scanned on the retina. A non-linear pixel clock can be used to determine when to receive the signal associated with the image of the portion of the retina of the eye.

In yet another aspect, there is a method for generating an image of the retina. The method includes tracking a reference feature of the retina of the eye, scanning an imaging beam along a first portion of the retina using a two-dimensional transverse scan, and controlling the position of the imaging beam relative to the reference feature to correct for motion of the eye. The method compensates for an optical distortion of an image of the retina by correcting the imaging beam scanned on the retina. A first signal is detected that is associated with a first image of the retina at a first plurality of points along the first portion of the retina. The method then positions the imaging beam according to a predetermined off-set to scan a second portion of the retina. A second signal is detected, associated with a second image of the retina at a second plurality of points along the second portion of the retina. A mosaic image of the retina is generated, including the first image of the retina at the first plurality of points and the second image of the retina at the second plurality of points.

In another aspect, there is a method for treating an eye. The method includes tracking a reference feature of a retina of the eye, scanning an imaging beam along a portion of the retina and controlling the position of the imaging beam relative to the reference feature to correct for motion of the eye. A signal associated with an image of the portion of the retina scanned is detected and an optical distortion of the image of the retina can be compensated for by correcting the imaging beam scanned on the retina. A target feature in the image of the portion of the retina scanned can be identified and a therapeutic beam can be delivered to the target feature to treat the eye. The therapeutic beam can be delivered such that delivering the beam is confined to the target feature.

In other examples, any of the aspects above, or any apparatus or method described herein, can include one or more of the following features.

In some embodiments, the first module includes a device for dithering a tracking beam in a first and second direction with an oscillatory motion having a first and second phase. A first tracking device can control the position of a beam relative to a target and controls the position of the tracking beam relative to the reference feature. The first tracking device can have a first input for accepting a first direction control signal and a second input for accepting a second direction control signal, causing the first tracking device to move the beam in the first and second direction. In some embodiments, the first module also includes a second tracking device for controlling the position of the imaging beam relative to a target. The second tracking device can also include a first input for accepting a first direction control signal and a second input for accepting a second direction control signal, causing the second tracking device to move the imaging beam in the first and second direction. In some embodiments, the first module also includes a reflectometer to provide an output signal with a phase corresponding to a phase of the reflected tracking beam. A signal processor can compare the phase of the reflectometer output signal to the phases of the oscillatory motion in the first and second directions. The signal processor can generate the first and second direction control signals for the first tracking device and for the second tracking device. The signal processor can be coupled to the first and second inputs of the first and second tracking devices, respectively. In some embodiments, the first and second direction control signals to the first tracking device cause the beam to track relative to the reference feature while the first and second direction control signals to the second tracking device cause the imaging beam to track relative to the reference feature. The second tracking device can be positioned at a pupil conjugate, a retinal conjugate or a conjugate to the center of rotation of the eye.

At least one scanner can be positioned at a center-of-rotation conjugate of the eye to substantially simultaneously track a pupil and the retina of the eye. A first scanner can be positioned at a pupil conjugate and a second scanner can be positioned at a center-of-rotation conjugate to translate the imaging beam.

In some embodiments, the first direction control signal and the second direction control signal sent from the signal processor to the second tracking device is filtered to vary at least one of the speed, accuracy and bandwidth of the respective tracking devices. The first direction control signal and the second direction control signal sent from the signal processor to the second tracking device can be scaled direction control signals sent to the first tracking device.

In various embodiments, a controller can be in communication with the first module, the second module, and the third module. The scanning device of the second module includes a first galvanometer and a second galvanometer. The controller delivers a first direction control signal to the first galvanometer and a second direction control signal to the second galvanometer to control a translational position of the imaging beam to track relative to the reference feature. The controller can receive, from the wavefront sensor of the third module, information relating to translational position of the eye to generate the first direction control and the second direction control. A controller can be used to relock a tracking beam of the first module on the reference feature after an eyelid passes across the reference feature and breaks tracking.

In some embodiments, a therapeutic beam in a common optical path with the imaging beam of the second module is used. The therapeutic beam can be a laser and can be an "ultra short" laser with a pulse duration of less than 1 microsecond. The laser can be delivered to treat the eye by targeting at least one of a retinal pigment epithelial cell, a feeder vessel, a drusen, a small tumor, a microaneurysm, and an epiretinal membrane. Any damage done to the eye can be confined and targeted to a specific feature of the eye by using an ultra short pulse duration of less than 1 microsecond. In some embodiments, at least one spherical mirror can be used to prevent dispersive pulse broadening for ultra-fast laser pulses. The second tracking device of the first module can be used to control the position of the therapeutic beam and/or imaging beam relative to a target. A stimulus beam can be used for vision studies.

In some embodiments, the scanning device of the second module performs a transverse two-dimensional scan of a focused spot of the light from the imaging beam on the retina of the eye such that the imaging beam reflected from the retina of the eye is received back and descanned in a common optical path. The scanning device can include a resonant scanner to scan a first portion of the retina of the eye and a galvanometer to reposition the resonant scanner according to a predetermined off-set to scan a second portion of the retina of the eye. In some embodiments, the signal processor of the first module generates first and second direction control signals which is coupled to the galvanometer, to control a translational position of the imaging beam relative to the reference feature. The signal processor of the first module can also send direction controls signals to the galvanometer to control the translational position of the therapeutic beam relative to a target. The second module may include at least one spherical mirror to compensate for distortions in the retina of the eye. At least one pair of spherical mirrors can be used to minimize astigmatism of the imaging beam.

In some embodiments, the second module can include a non-linear pixel clock associated with the first detection device. The non-linear pixel clock can be used to determine when to receive the signal associated with the image of the portion of the retina of an eye as the scanning device moves the imaging beam along a portion of the retina of the eye.

In some embodiments, the first module has an imaging apparatus wherein the beam is a second imaging beam. In yet another embodiment, the first module can be used to provide a wide-field optical image and the second module provides a narrow-field optical image of a feature of the wide-field optical image. The first module can be a line scanning laser ophthalmoscope to provide a wide-field optical image. The second module can be a confocal flying spot scanning laser ophthalmoscope to provide a narrow-field optical image or a spectral domain optical coherence tomographer to provide a narrow-field optical image. In some embodiments, the source for the imaging beam and the second imaging beam is a superluminescent diode. A broadband superluminescent diode can reduce speckle noise in an SLO image.

In some embodiments, the wavefront sensor of the third module uses another beam called a beacon which uses the same double-pass optical path as the imaging beam. In some embodiments, the wavefront sensor of the third module receives a portion of the imaging beam of the second module reflected from the retina of the eye and detects the distortion of the retina of the eye. The wavefront compensator can be an adaptive optical element and can be a deformable mirror. The deformable mirror can be such that the z-position of portions of the mirror can be independently controlled to provide any possible wavefront representation.

In some embodiments, a retina is imaged by receiving the signal associated with the image of the retina while scanning the imaging beam along a portion of the retina. In another embodiment, the method for generating a mosaic image of the eye includes averaging a plurality of images of the first image of the first portion and second portion of the retina to improve signal to noise ratio.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 5 shows FIGS. 5A, 5B and 5C.

DETAILED DESCRIPTION OF THE INVENTION

Figure 1:
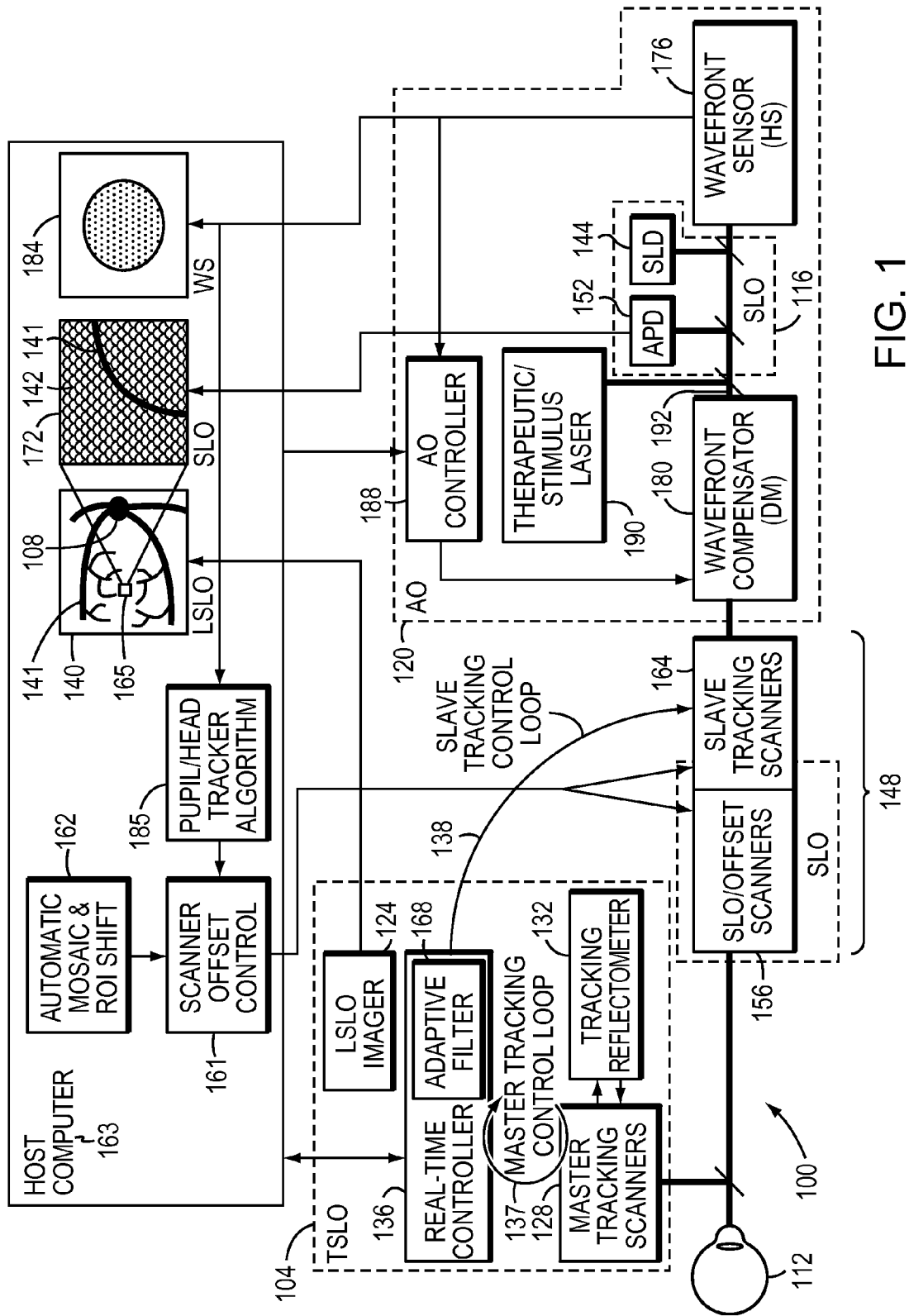
FIG. 1 is a schematic drawing of an illustrative embodiment of the apparatus.

FIG. 1 shows an illustrative embodiment of a retinal imaging system 100 including three subsystems: a first module 104 for retinal tracking, a second module for imaging 116, and a third module with adaptive optics 120. The first module or retinal tracker 104 can stabilize to fixed and repeatable retinal coordinates and correct for the adverse effects of eye 112 motion. The retinal tracker 104 can include a wide-field line-scanning laser ophthalmoscope (T-LSLO, or TSLO). The second module or imaging apparatus 116 can be a flying-spot scanning laser ophthalmoscope 116, which can provide high-magnification confocal images. The third module or adaptive optics (AO) component 120 can sense wave-front distortion and correct for ocular aberrations.

Control of hardware and acquisition and processing of images and data from the sub-systems can be accomplished using a single software platform. The system, therefore, can present to the operator and/or clinician a wide-field view of a large portion of the retina, a high magnification view of a particular region of interest, and a view of the ocular aberrations in both the raw form of wave-front slopes and the refined form of wave-front error map and Zernike coefficient plot. The SLO subsystem can create an image by detection of a flying-spot raster focused on the retina in a confocal arrangement. The adaptive optics component can use a Hartmann-Shack wave-front sensor and deformable mirror to detect and correct ocular aberrations in a closed loop. The system also includes a port that can be used for delivery of near-diffraction-limited stimulus or therapeutic beams to the retina. The stimulus or therapeutic beam can require an external independent focus and are collimated into the port behind the deformable mirror.

Referring to FIG. 1, the retinal tracker 104 can track a reference feature 108 shown in a wide-field image 140 of the retina of an eye 112. The reference feature 108 can be the optic nerve head. Other features of the eye that can be used as the reference feature 108 include features of the fundus, such as blood vessel junctions, scleral crescents, foveal pits, and regions of hypopigmentation in a subject with a diseased eye. Other features of the eye shown in the image 140 include blood vessels 141. In some embodiments, the retinal tracker 104 includes a second imaging apparatus 124, such as the TSLO, to provide the wide-field image 140. The retinal tracker 104 can include a first tracking device 128 for controlling the position of a tracking beam relative to the reference feature 108 and for controlling the position of second imaging beam associated with the second imaging apparatus 124. A reflectometer 132 can provide an output signal with a phase corresponding to a phase of the reflected tracking beam, and a signal processor 136 can compare the phase of the reflectometer output signal to the phases of the oscillatory motion in the first and second direction, generating the "master" tracking control loop 137. The retinal tracker 104 can stabilize high magnification images by driving two galvanometers 164 placed at appropriate conjugates within the path of the retinal imaging system 100 in a "master-slave" configuration. The input to the master control loop 137 is x-y error signals generated from the low power track beam (~100 μW measured at the cornea, 1060-nm laser diode, LD) dithered on a retinal feature and detected from a confocal reflectometer 132. The input to the slave control loop 138 is the scaled position signals from the master galvanometers 128. The slave tracking mirrors 164 are placed at conjugates to the center of rotation of the eye. This allows line-of-sight tracking (i.e., simultaneous tracking of the pupil and retina from rotational eye motion) because the mirrors pivot about the true axis of rotation of the eye 112.

Integration of retinal tracking into the retinal imaging system 100 in a master-slave configuration requires several considerations. The setup requires a one-time calibration (gain and offset) between master and slave mirrors. To allow for tracking on a number of potential targets, it is desirable to make the fields of view of the tracker and AO systems disparate. Thus, targets can be tracked anywhere within greater than about the 40 deg LSLO field while the AOSLO is designed with optics to produce little distortion over a smaller field (about less than a 15 deg field).

The galvanometer control electronics can be scaled to the appropriate angular range to maximize dynamic range. The lamina cribrosa in the optic disc can be tracked, and imaging can occur near the fovea, e.g., features separated by about 15 deg. This separation results in geometric and torsional eye motion errors because the eye rotates about equatorial axes and cyclo-rotates about an axis centered near the posterior pole. The one-time calibration between master and slave eliminates geometric, but not cyclo-rotational, errors. The TSLO 104 can produce a wider field of view at the expense of increased aberrations that are small relative to the pixel size. Aberrations can be carefully minimized in the AOSLO path due to the high resolution and small pixel size. Therefore, the AOSLO raster cannot pass through the wide-field LSLO imaging optics and can be combined at the pupil in a different manner.

Nested pupil tracking can result from adjusting the offsets of the slave and AOSLO raster scanners in a coordinated manner. Because these mirrors are at different conjugates, walking these mirrors within limits with commands derived from both retinal and pupil coordinates (the latter from the HS-WS) can correct for translational head motion. Eye motion is generally rotational, while head motion is generally translational. The combined residual error over AO image sequences can be examined with retinal tracking alone in order to estimate the magnitude of pupil translation effects.

The tracking functions can be performed by a single set of stacked electronics boards. A single printed circuit board can also be used. Communication between the tracking board(s) and host computer is accomplished via a USB interface. Control parameters are passed to and reflectance, position, and error signals are received from the tracking board(s). A blink detection and track re-lock algorithm can be used. The control and processing electronics include a field programmable gated array (FPGA) chip that performs digital lock-in amplification and other pre-processing steps, a digital signal processor (DSP) that performs two proportional-integral-derivative (PID) control loops (for master and slave systems), and analog-to-digital and digital-to analog converters (ADC and DACs) to receive reflectometer signals and drive galvanometers. The DSP has a loop rate of about 62.5 kHz for a closed loop bandwidth well in excess of 1 kHz. The tracking beam wavelength can be in the 800-900-nm range, or can be 1060 nm to accommodate typical superluminescent diodes (SLD) used in SLO and optical coherence tomography (OCT) systems. Other tracking beam wavelengths can be used as well. The resonant scanner—and dither frequency—can be 8 kHz or 16 kHz, although other frequencies can be used.

An exemplary LSLO system is described in U.S. Pat. No. 6,758,564, the disclosure of which is herein incorporated by reference in its entirety. The LSLO can be combined with a retinal tracking system to form a TSLO. An exemplary tracking system is described in U.S. Pat. No. 5,797,941, the disclosure of which is herein incorporated by reference in its entirety.

The imaging apparatus of the second module 116 has a source 144 for an imaging beam, a scanning device 148 to move the imaging beam along a portion of the eye 112, and a first detection device 152 to receive a signal associated with an image of the portion of the object. In some embodiments, the scanning device 148 includes a resonant scanner to scan a first portion of the eye 112 and a galvanometer 156 to reposition the resonant scanner. The galvanometer can reposition the resonant scanner 156 according to a predetermined off-set to scan a second portion of the retina of the eye 112. The offsets of the scanners 156 and 164, positioned at the pupil conjugates and center-of-rotation conjugates, can be controlled using a scanner offset controller 161. The imaging beam for the second module can be moved to any region-of-interest 165 in the wide field with the scanners by the host processor 162. The offset controller 161, the host processor 162, the pupil/head tracker algorithm, and displays for the images 140, 172, 184 can be part of a host computer 163. In some embodiments, the host computer 163 can include framegrabbers and data acquisition boards associated with the host computer 163 components. The host computer 163 can control the computer hardware, communicate with the retinal tracking board, and process data from the wavefront sensing. The host computer 163 can also be involved in adaptive optic control, image and signal acquisition and processing, image averaging, and source modulation. The off-set scanner can be used to form a mosaic image of the eye 112. The imaging apparatus 116 can be a SLO and create an image by scanning a flying spot on the retina and de-scanning through the same optics back to a confocal pinhole. Unequally-sized entrance and exit pupils can be used. The retinal tracker 104 can control the position of the imaging beam relative to the reference feature 108 to correct for motion of the eye 112.

In some embodiments, the first module 104 has a second tracking device 164, which can include a first input and a second input. The first input can accept a first direction control signal from the signal processor 136, and the second input can accept a second direction control signal from the signal processor 136, causing the imaging beam to track relative to the reference feature 108. In some embodiments, an adaptive filter 168 filters the direction control signals sent from the signal processor 136 to the second tracking galvanometers 164. The adaptive filter 168 can be used to vary the bandwidth of the respective tracking devices. In some embodiments, the second tracking galvanometers 164 and the offset galvanometers 156 are positioned at a pupil conjugate, a retinal conjugate, or a conjugate to the center of rotation of the eye.

In some embodiments, the second tracking device is a galvanometer. The processor can use the image 184 generated by the wavefront sensor 176 and apply a pupil/head tracker algorithm 185 to sense and calculate translational pupil and head position. In some embodiments, a processor 161 can send direction control signals to the galvanometers 156 driving the offset of the resonant scanners, causing the imaging beam to track translationally relative to the reference feature.

For example, the master tracker can use a reflectometer error signal generated from phase-sensitive detection of the dithered tracking beam in a control loop (e.g., elements 128, 132, and 136). For slave tracking operation, a separate control loop can be run that uses the positions of the master galvonometers as the input. The adaptive filter 168 can provide calibration and filtering to the slave galvonometer 164. Mirrors can be placed at both the pupil and center-of-rotation conjugates. The offsets of at least one or all of the scanners, including the resonant scanner, can be adjusted. Therefore, a scanner can be moved to any angle. Direction control signals can drive the offset of the resonant scanner, causing the imaging beam to track translationally relative to the reference feature.

The imaging apparatus 116 can provide a narrow-field image 172 of the eye 112. The narrow-field image 172 can include features such as blood vessels 141 and cones 142. The source 144 for the imaging beam can be a laser or a superluminescent diode. A superluminescent diode can provide a broadband output and reduce speckle noise. The scanning device 148 can perform a transverse two-dimensional scan of the eye 112.

The third module 120 of the retinal imaging system 100 includes a wavefront sensor 176 to detect an optical distortion of an image of the retina and a wavefront compensator 180 to correct for the optical distortion. The wavefront sensor 176 can generate image data 184 of the eye 112 based on the optical distortions of the eye 112. The sensor 176 of the third module 120 can include a Hartmann-Shack wavefront sensor, receiving a first portion of the imaging beam of the imaging apparatus 116 reflected from the eye 112 and detecting the distortion of the eye 112. The wavefront compensation device 180 can be an adaptive optical element for correcting for the distortion in the imaging beam scanned on the eye 112 and for correcting the distortion in the imaging beam reflected from the eye 112. The wavefront compensator 180 can be a deformable mirror to detect and correct ocular aberrations. In some embodiments, a processor 188 analyzes the image data 184 generated by the wavefront sensor 176 and controls the compensator 180 to correct for the distortion of the object. In some embodiments, the processor 188 can be an adaptive optics controller.

The SLO flying-spot raster can be accomplished using a 12-kHz resonant scanner in the fast x-axis and a galvanometer in the slow y-axis. These mirrors can be placed at pupillary conjugates to pivot the retinal scan from a stationary beam at the pupil. The resonant scanner 156 can be attached to the galvanometer. This configuration, where offsets can be applied to galvanometers along both axes of the raster, allows advanced scans to be created (e.g., 4-5-deg macular montage pieced together automatically from single SLO frames). A near-infrared source 144 (e.g., a 830-nm laser diode or an 800-nm SLED with 30-nm bandwidth available from Exalos Inc.) can be used for SLO illumination. The detector 152 can be an avalanche photodiode detector (available from Hamamatsu Inc.) with confocal pinhole (e.g., 100 and 200- µm diameter).

The AO system can include a Hartmann-Shack wave-front sensor (HS-WS) having a 65×65-element lenslet array (e.g., having a 0.4-mm pitch and 25-mm focal length, available from Adaptive Optics Associates Inc.) and a 1024×1024- pixel CCD camera with a maximum frame rate of 60 Hz and camera-link interface (Dalsa Inc.). Wavefront sensing can be performed using a 670-nm AO beacon. The beacon can be placed in front of the deformable mirror (DM) to minimize distortion from mirror surface irregularities and to de-couple mirror-induced wavefront errors during mirror-sensor calibration. It can be placed behind the scanning mirrors to provide smoother spots and improve the accuracy of the centroid algorithm. A 141-element MEMS-based, continuous-surface, electrostatic-actuator-driven deformable mirror (available from Boston Micromachines Inc.) can be used for wavefront correction. The deformable mirror can have a diameter of only 4.8-mm so long paths are not required to magnify the pupil.

The optics can be designed to de-magnify a 6-mm pupil through the small resonant scanner mirror, to fill the DM (to use all actuators) and magnify again to nearly fill the WS camera. Spherical mirrors can be used to limit back reflections, minimize chromatic distortion, and, since the system will be used to deliver short pulses to the eye, minimize dispersive pulse broadening. Spherical mirrors used off-axis can induce astigmatism in the beam. To compensate, focus adjust of up to 10 diopters can be achieved with two stages: one on which the system is placed that controls the space between a front lens relay (e.g., a system designed to minimize spherical and chromatic aberrations and control field flatness), and a second smaller stage that adjusts the position of the DM within the system. TSLO focus can be adjusted independent of the AOSLO focus. The AOSLO optical design achieves an error of <0.45 waves (at 800 nm) over ±6 deg on the retina including front lens relay.

The LSLO source for wide-field imaging can be a 905-nm SLED. The combined power of the four wavelengths that enter the eye—670, 830, 905, and 1060-nm for the AO beacon, SLO beam, LSLO beam, and tracking beam, respectively—can be maintained below ANSI standard thresholds. Typical powers used are 35, 300, 200, and 100 µW, respectively.

Three frame grabbers can be used (e.g., an analog for SLO, a digital camera-link for WS, and a digital for LSLO), A timing board can provide a non-linear pixel clock to the analog framegrabber to linearize the sinusoidal scan of resonant scanner. This board can also provide vertical and horizontal sync signals to the framegrabber, to the SLO LD/SLD for modulation, and to the "Exsync" signal of the WS camera-link framegrabber. The modulation creates a blanking region for the analog framegrabber. A physical mask placed in the optical train cannot be used to create a blanking region while the retinal tracker operates because the raster is moved about the field as the eye moves. Synchronization between the SLO and WS frames assures congruency between each WS slope and the retinal coordinate of the corrected AOSLO image. Wave-front correction can be insensitive to errors from a lack of eye isoplanicity, although this contribution to wave-front distortion is small and the cameras can be run asynchronous.

The LSLO 104 and SLO 116 systems are typically not synchronized since they use optical paths independent of one another. The LSLO camera can acquire a 512×512-pixel frame at 15 frames/sec. The 12-kHz resonant frequency of the SLO scanner can enable a 512×512-pixel frame rate up to about 25 frames/sec. A speed can be selected so that the images from all three components (LSLO 104, SLO 116, and WS 120) are acquired and displayed by a single software platform. In addition to acquisition, display, and processing of the three images, the software controls communication with the tracking board, WS spot position and slope calculation, AO (WS/DM) calibration, AO closed-loop operation, wave aberration and Zernicke coefficient calculation and display, and logging of tracking signals, AVI videos (from the three cameras), and single images in a variety of formats. A live video can be streamed to disk, and two additional files can be saved that contain track data (reflectance, x-y track mirror positions, and either the x-y error signals or the x-y slave mirror positions) in binary format and a text file that contained all system parameters and calibration factors in a text format.

For AO-correction using the continuous-surface DM, a one-time calibration can be performed subsequent to system alignment to find the influence of each actuator on its neighbors and to establish a baseline for calculation of slopes. The software can use a standard algorithm for spot centroid determination that operates at the frame rate of the WS camera (e.g., up to 30 Hz). During AO-correction, the local wavefront slopes are found and inverted with a pseudo-influence function and fed to the DM driver. The wave aberration function and Zernicke coefficients can be calculated in real-time. The closed-loop bandwidth of the AO system is about 2-3 Hz.

In some embodiments, the retinal imaging system 100 includes a source 190 of a beam 192 of radiation, which can be delivered to treat or stimulate the retina, or a portion thereof, of the eye 112. The beam 192 can be near-diffraction-limited. For example, the beam 192 can be a therapeutic beam delivered to the eye 112 to treat a target feature of the retina. The target feature can be a retinal pigment epithelial (RPE) cell, a feeder vessel, a drusen, a small tumor, a microaneurysm, or an epiretinal membrane. The retinal imaging system 100, with an SLO imager or a OCT imager, can provide a high resolution, near field image of the target feature, and the beam 192 can be delivered to precisely target and treat the target feature.

In some embodiments, the beam 192 is a near-diffraction-limited stimulus beam that can be used for vision studies. The beam 192 is delivered to the eye 112 so that measurements of the eye or the retina can be recorded. In some embodiments, the second tracking device 164 can control the position of the beam 192 and the imaging beam relative to a target feature.

The beam 192 can be a coherent beam of light (e.g., generated by a laser) or an incoherent beam of light (e.g., generated by a pulsed light source or a light emitting diode). In some embodiments, the pulse duration of the source is less than about 1 μsec. For example, the beam 192 can have a pulse duration in the femto, pico, or nano second time regime. The laser can be an ultra short pulsed laser, which can confine thermal injury to the target feature and avoid unwanted damage to surrounding tissue.

In some embodiments, the beam 192 is collimated into a port or coupled into the system using an optic positioned behind the wavefront compensator 180. The beam 192 can require an external independent focus. The beam 192 can be inserted into the system behind the deformable mirror and behind the slave tracking mirrors to correct for (a) ocular (or optical) distortions that can occur in this beam are removed and (b) eye motion that can prevent the beam from being locked to fixed retinal coordinates. Thus, a diffraction-limited spot can be delivered to confined, precise, and fixed coordinates on the retina, features that can not be performed without retinal tracking and AO. Using an ultra-short pulsed device can further confine the damage.

Furthermore, AO and ultrashort pulse delivery not only give precision in lateral coordinates, they give the ability to confine your focus and damage along the axial dimension. AOSLO systems have a very narrow depth of focus and ultrashort pulse damage is mediated by non-linear mechanisms that are intensity dependent and hence inherently confined to the axial region where the intensity is highest.

Figure 2A:
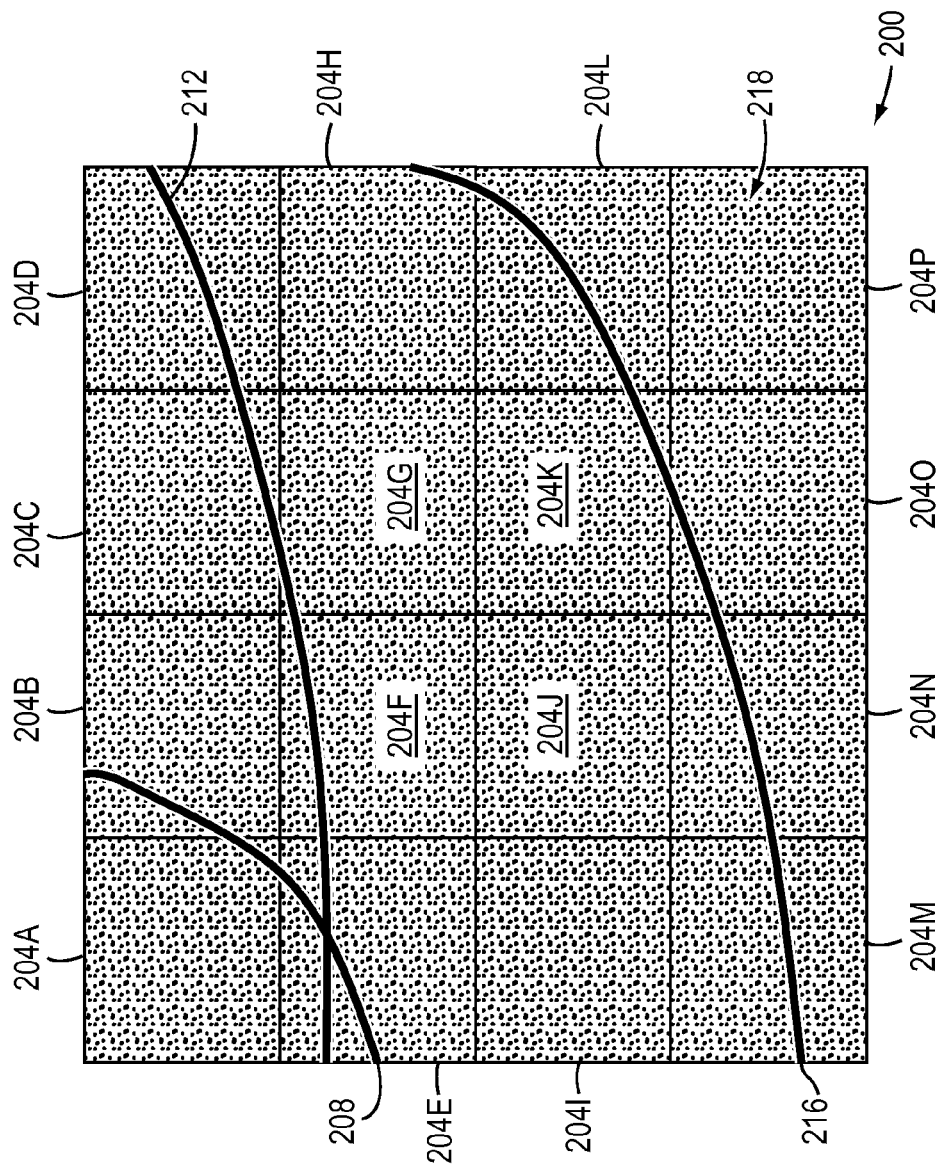
FIG. 2A is an exemplary automated montage of an object comprised of images generated by an illustrative embodiment of the apparatus.

FIG. 2A shows a montage or mosaic 200 of images 204A-P of an eye generated using a retinal imaging system. For adaptive optics systems, the high magnification necessary to resolve small structures is concomitant with smaller fields. Use of a retinal imaging system 100, therefore, can generate a high-magnification image of an eye (or a portion of the retina) over a wider field by compiling several narrow-field images 204A-P. In some embodiments, the montage 200 can provide a high-magnification image of the eye over a wide field that includes several reference features such as veins 208, 212, 216 or cones 218.

A montage or mosaic image 200 can be created using a scanning device 148 of the imaging apparatus 116. For example, the scanning device 148 includes a scanner 156 and a driver. The scanner 156 can be a resonant scanner that scans a first portion of the eye (e.g., a first portion of the retina) and the driver can be a galvanometer that repositions the resonant scanner on a second portion of the eye (e.g., a second portion of the retina) according to a predetermined off-set. Thus, a first image (e.g., image 204A) can be acquired by the imaging apparatus 116 when the resonant scanner 156 scans the imaging beam along on the first portion of the eye. The scan can be a raster scan or a two-dimensional transverse scan. A second image (e.g., image 204B) can be acquired by the imaging apparatus 116 after the galvanometer repositions the scanner on the second portion of the eye. The process can be repeated to acquire images 204C-P over the other portions of the eye until the montage 200 has been generated.

Figure 2B:
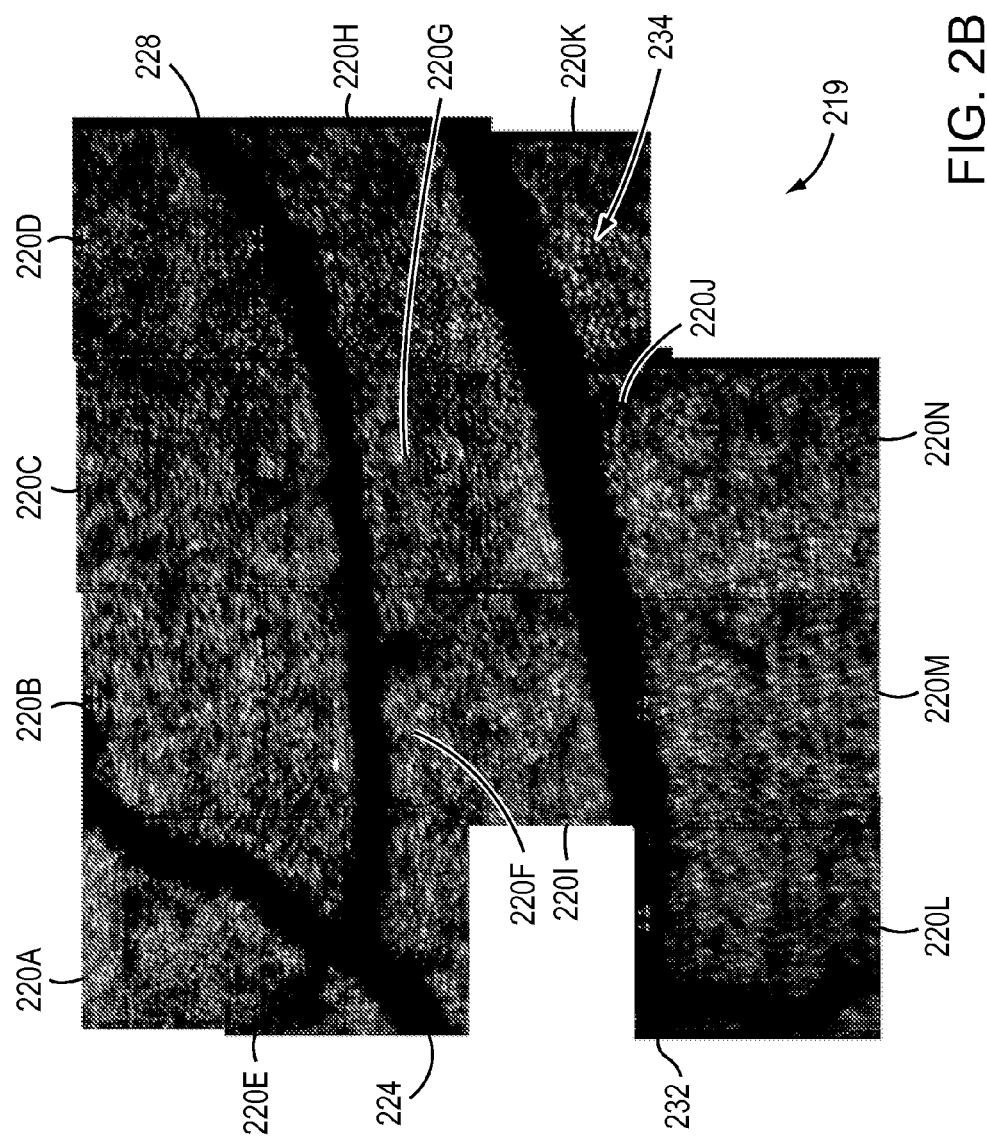
FIG. 2B is an automated montage of an object comprised of actual images of a test subject generated by an illustrative embodiment of the apparatus.

FIG. 2B shows an automated montage or mosaic image 219 including actual images 220A-N acquired from an eye of a test subject. The narrow-field images 220A-N show small structures of the eye, such as veins 224, 228, 232 and cones 234 (the white dots in the background).

Figure 3:
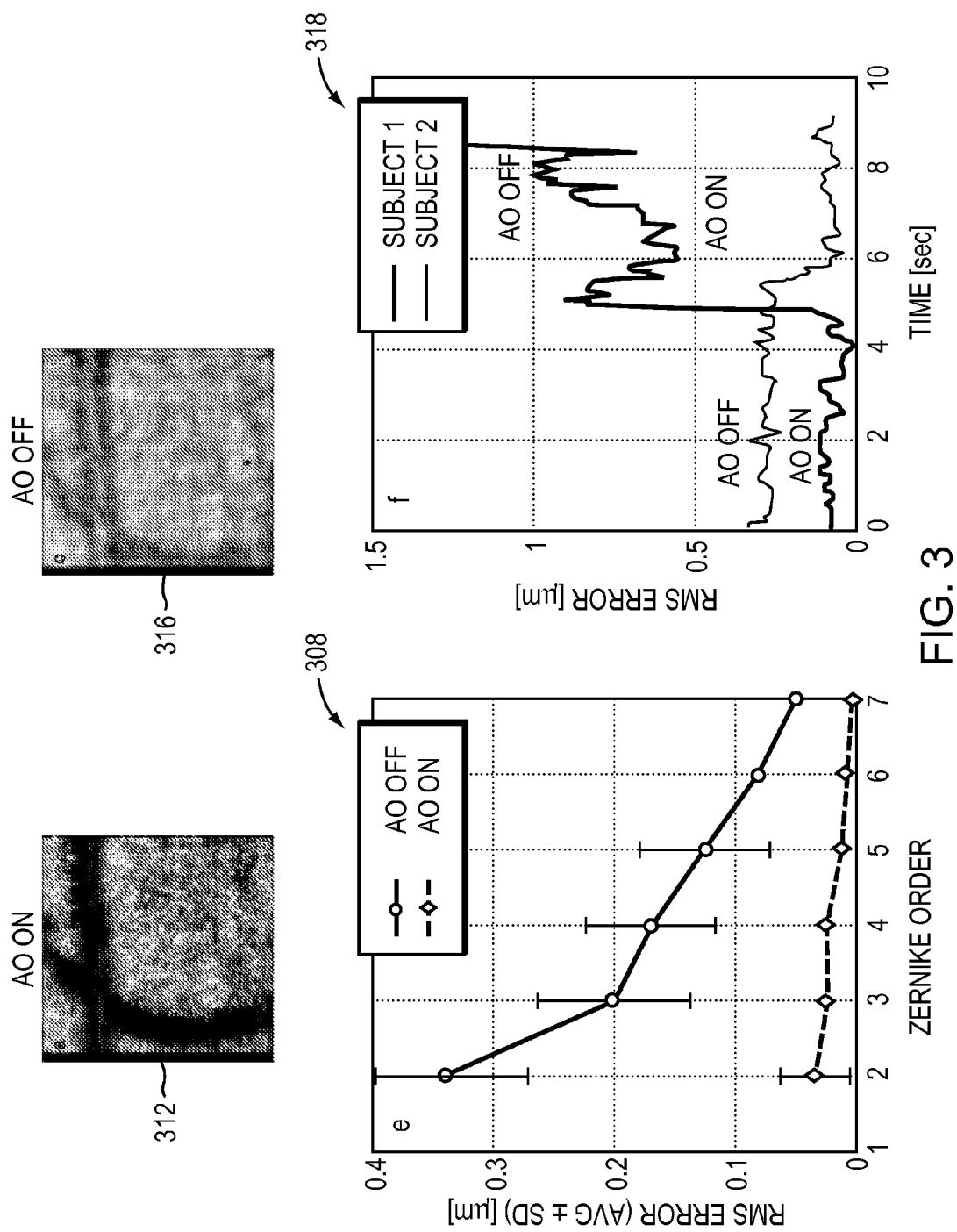
FIG. 3 is a comparison of the performance of an illustrative embodiment of the apparatus with the use of a compensator to correct for distortions versus the performance of an embodiment of the apparatus without the use of a compensator.

FIG. 3 represents the performance of a retinal imaging system with and without the use of an adaptive optics module. A Hartmann-Shack wavefront sensor and a deformable mirror compensator were used to correct for wavefront aberrations. Videos were acquired using the retinal imaging system to characterize the performance of the sensor and compensator to dynamically correct distortions. A wave-front error map (full scale=±2 μm) was averaged over those video frames acquired with and without AO correction, respectively. The mean (min-max) root mean square (RMS) error was 0.08 (0.02-0.13) μm with AO correction and 0.78 (0.55-1.16) without AO correction. Graph 308 shows the RMS error separated by Zernike order and also averaged over corresponding frames acquired with and without correction. Graph 308 indicates that both lower and higher order aberrations are corrected by the correction system.

Images 312 and 316 demonstrate another quantitative measure of AO improvement. Image 312 was obtained with the use of the sensor and compensator while image 316 was not. When measured in a region of interest (ROI) that measured 50×50 pixels in the center of the image, the Michelson contrast increased from 0.20 to 0.50. Another measure of contrast improvement is the standard deviation of the image histogram, which increased from 37.9 to 52.4 when measured across the entire and nearly doubled when measured in an ROI that included only cones from 23.9 to 40.3. Graph 318 shows the AO correction as a function of time for a first subject and for a second subject with lower uncorrected ocular aberrations (with a 5-mm pupil). The mean (min-max) RMS error for subject 2 was 0.09 (0.04-0.14) μm with AO correction and 0.29 (0.24-0.35) without AO correction. For subject 1, the video was acquired with the AO on and then off and vice versa for subject 2 so only the data on subject 2 yielded a meaningful rise-time and hence AO closed-loop bandwidth. The 10%-90% rise-time measured for subject 2 was 0.36 sec for a measured closed-loop bandwidth of about 2.8 Hz.

The SLO imaging beam can be scanned in a flying-spot raster pattern that can use a high speed scanning device, such as a resonant scanner. Resonant scanners can have a higher duty factor than other types of high speed scanners, such as spinning polygons. These scanners are driven at their resonant frequency, and their scan pattern is typically sinusoidal. The scanner has a relatively constant speed in the middle of the scan, but slows down at the ends of the scan before turning around and speeding up again in the opposite direction. An imaging beam scanned in this manner can produce a distorted image (spread out at the ends). This problem can be rectified by cropping the image to the linear portion of the scan or by post-processing routines that are time consuming and do not allow direct visualization of optimal images. Therefore, an analog frame-grabber can be synchronized real-time to this non-linear sinusoidal scan. A line synchronization signal is received from the resonant scanner and generates a non-linear pixel clock. The number of pixel clocks per resonant scanner cycle is set prior to acquisition and determines the number of horizontal image pixels. The phase between the driven resonant scanner waveform (and line synchronization signal) and the pixel clock can be adjusted. By adjustment of the framegrabber pixel clock in this manner, each image pixel essentially collects light from equivalently-sized patches of retina despite a scanner that speeds up and slows down, and image distortion is removed in real-time.

Figure 4:
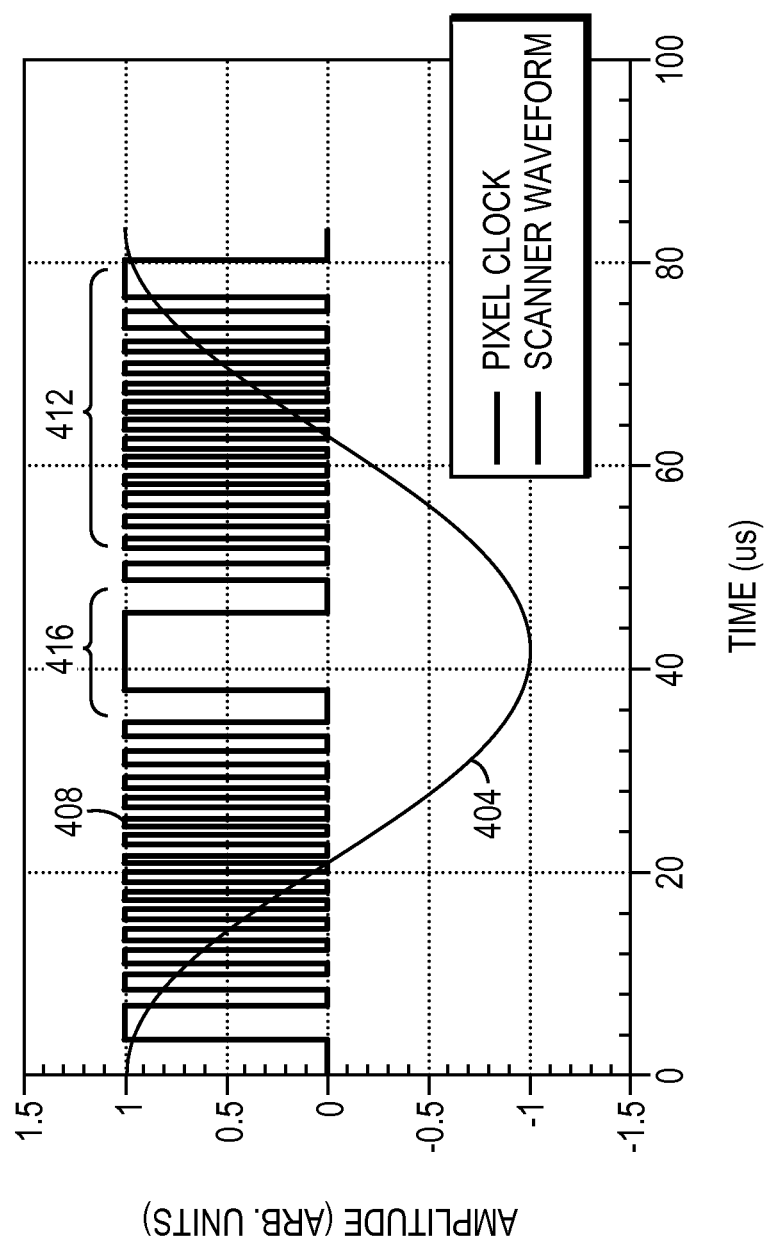
FIG. 4 is a graphical representation of the non-linear pixel clock according to an illustrative embodiment of the apparatus.

FIG. 4 shows the position 404 of a scanning device (e.g., scanner 148) over time during a sinusoidal scan. Other scan algorithms can be used. A galvanometer 160 can reposition a resonant scanner 156 according to a pre-determined offset to generate the sinusoidal scan of the eye. Points 408 show the points along the scan 404 when an image is received by a detection device. By utilizing a non-linear pixel clock, the detection device can acquire images more frequently at the linear portions 412 of the sinusoidal scan and at regular intervals in the non-linear portions 416 of the sinusoidal scan. The non-linear pixel clock linearizes the sinusoidal scan of the imaging beam and improves image quality and enables mosaic or montage images to be formed.

Figure 5A:
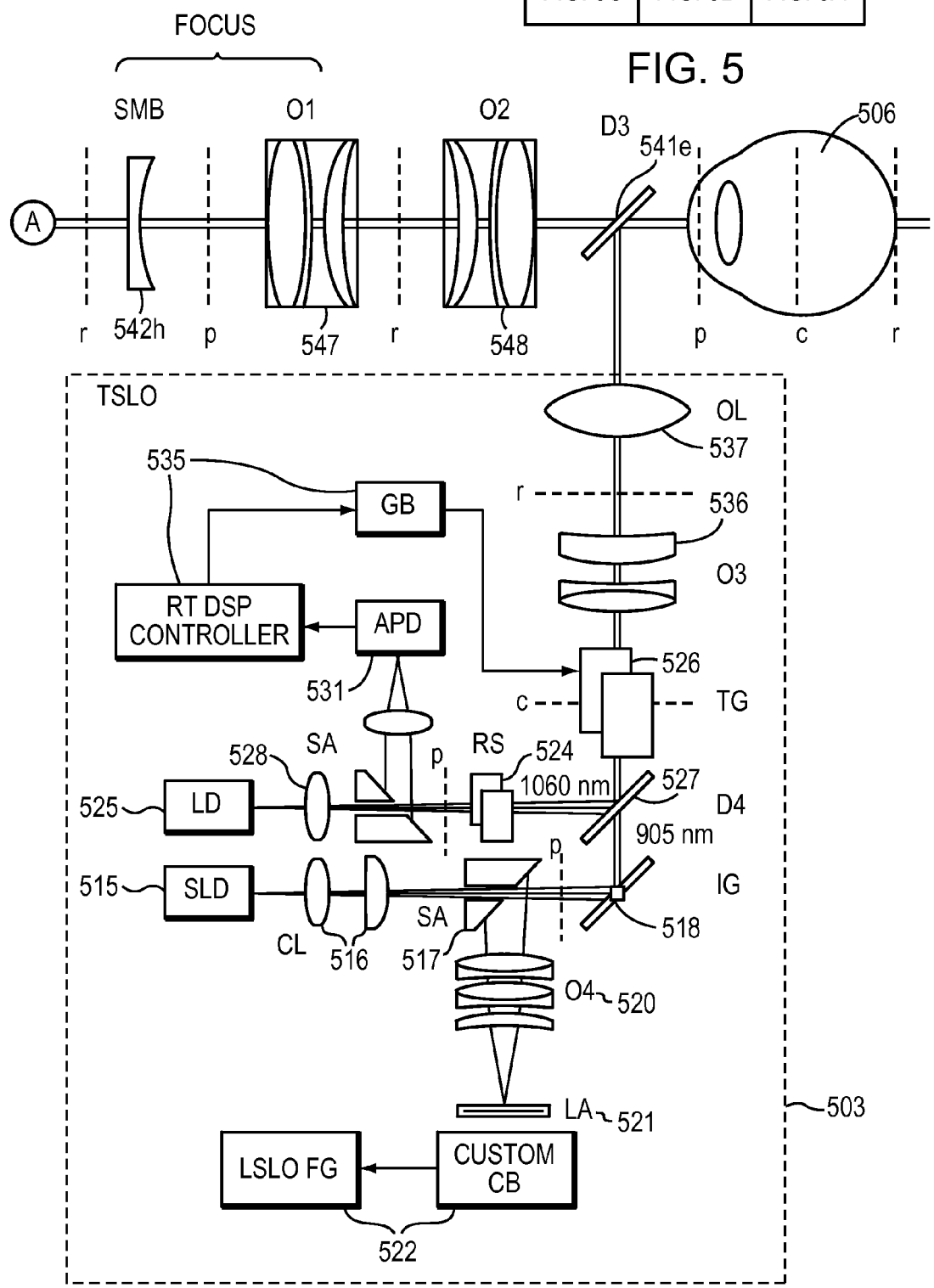
FIGS. 5A-5C show an optical layout of an illustrative embodiment of the apparatus.
Figure 5B:
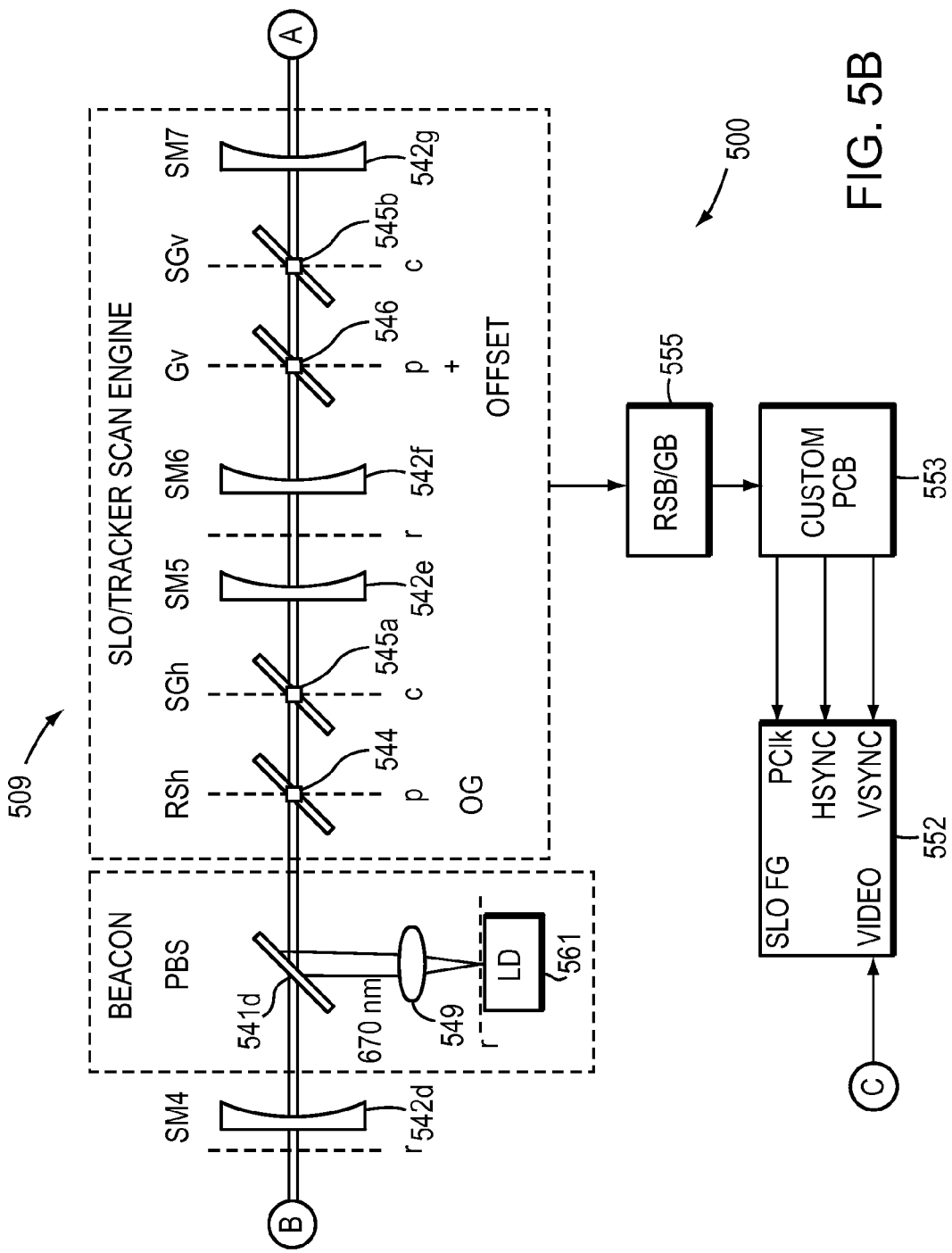
Figure 5C:
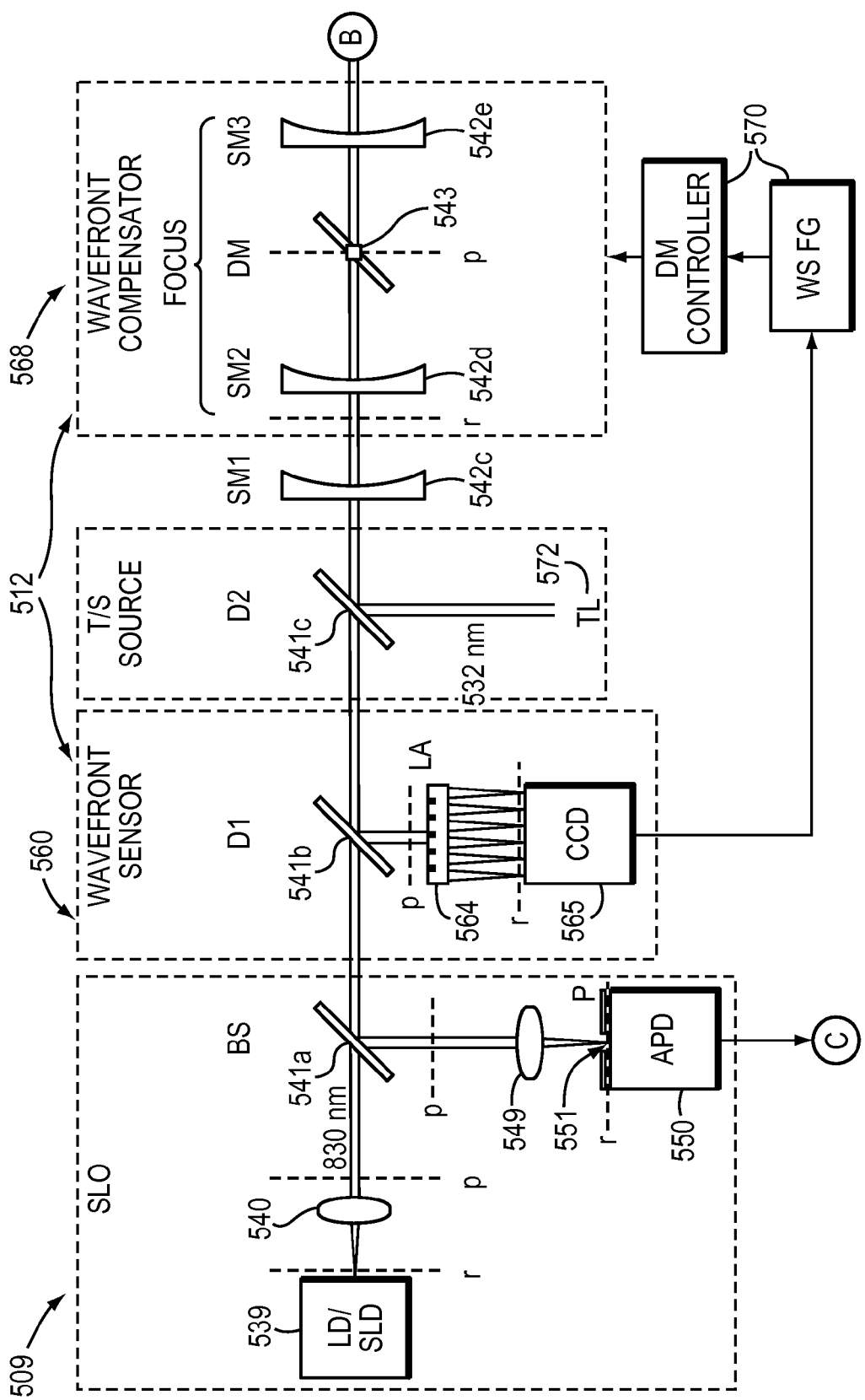

FIGS. 5A-5C demonstrate an optical layout of an embodiment of a retinal imaging system 500, which includes a first module 503 to track a reference feature of an eye 506, a second module 509 to generate an image of a portion of the eye 506, and a third module 512 to detect and correct an optical distortion of an image of the eye 506.

The first module 503 includes a line scanning laser ophthalmoscope for wide-field images. The LSLO includes a source 515 for a second imaging beam, a system of lenses 516 to form the point source to a line of light, a beam separator 517 with aperture to separate the scanned beam from the descanned beam, a galvanometer driven mirror 518 to scan the imaging beam along a portion of the eye 506, and an objective lens 520 to focus radiation returning from the eye to a linear array detector 521 to acquire a wide-field image of a portion of the eye. The detector 521 is in electrical communication with a framegrabber 522 for acquiring a plurality of images of the eye 506. The first module 503 includes a dithering device 524 (e.g., a resonant scanner) to dither a tracking beam provided by source 525 in a first and second direction with an oscillatory motion on the eye. In some embodiments, the dithering device 524 can be a resonant scanner. The first module also may have a first tracking device 526, such as a galvanometer, to control the position of the tracking beam and the second imaging beam associated with the LSLO. The tracking galvanometer can be placed at the conjugate associated with the center of rotation of the eye. The resonant scanner can be placed at or near the retinal conjugate. The beam paths of the retinal tracker and the LSLO can be combined with a beam splitter 527.

The source 525 for the tracking beam passes through a lens 528 and through the aperture of beam separator 529. A lens 530 focuses the return beam to an avalanche photo detector 531 in electrical communication with a signal processor or controller 535 that can send direction control signals to the first tracking device 526. Lens 536 and 537 focus the imaging beam and the tracking beam to the eye 506.

The SLO imaging apparatus provides narrow-field images. The SLO includes a source 539 for an imaging beam, which passes through a focusing lens 540, beams splitters 541*a-e*, spherical mirrors 542*a-h*, deformable mirror 543, resonant scanner 544 (which can include an off-set galvanometer), horizontal and vertical slave tracking galvanometers 545*a*, 545*b*, a raster galvanometer 546, and objective lenses 547, 548. In some embodiments, the source 539 for the imaging beam is a superluminescent diode. Beams splitter 541*a* directs light returning from the eye to a lens 549 that focuses the light to a detection device 550 to acquire images of the eye 506. In some embodiments, the detection device 550 includes an aperture 551. The detection device 550 is in electrical communication with a framegrabber 552 for acquiring a plurality of images of the eye 506. A timing board 553 can provide signals according to a non-linear pixel clock. A processor 555 can be used to average a plurality of images of the eye to improve signal to noise ratio.

Resonant scanner 544 and raster galvanometer 546 can be placed at pupil conjugates. Slave galvanometers 545*a*, 545*b* can be placed at conjugates associated with the center of rotation of the eye. Spherical mirrors 542*x* can compensate for distortions in the retinal imaging system, such as astigmatism of the beam. In some embodiments, an adaptive filter may be used to send direction control signals to one or more of the tracking galvanometers 545*a*, 545*b* to vary the speed, accuracy and/or bandwidth of the first tracking galvanometers 526 and/or the second tracking galvanometers 545*a*, 545*b*.

The third module 512 can detect and correct for optical distortions in the image of the eye 506. The light for the wavefront sensor 560 includes a source 561, a lens 562 to focus the source beam and a beam splitter 541*d*. The source 561 can be a laser diode or a luminescent diode. The wavefront sensor 560 includes a lenslet array 564, and a detection device 565. Light returning from the eye is reflected by beam splitter 541*b* into the wavefront sensor detection device 565. In some embodiments, the wavefront sensor 560 is a Hartmann-Shack sensor. The lenslet array 564 can generates a focused spot array from the light reflected from the eye, and the detections device 565 can be a CCD camera that acquires an image of the focused spot array.

The wavefront sensor 560 is in communication with the wavefront compensator 568 via a processor and deformable mirror controller 570. The deformable mirror 543 can be such that the z-position of portions of it can be independently manipulated by a controller to provide any possible wavefront representation. The deformable mirror 543 can be placed at the pupil conjugate.

In some embodiments, the system 500 includes a source 572 for a therapeutic or stimulus beam, which can be directed to the eye by beamsplitter 541*c*.

Figure 6:
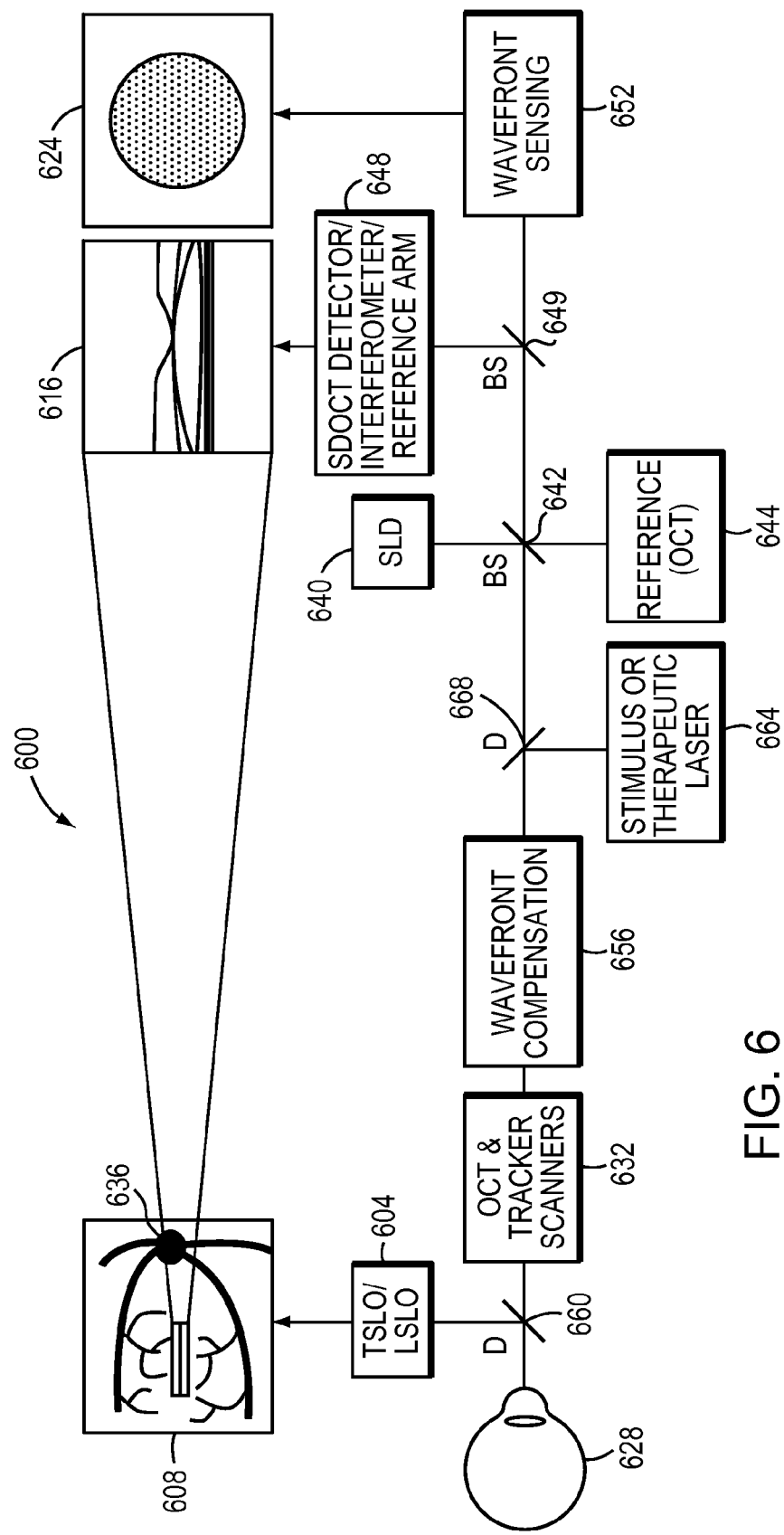
FIG. 6 is a schematic drawing of another illustrative embodiment of the apparatus.

FIG. 6 is a schematic of the optical layout of the retinal imaging system 600 that includes three main components: a first module 604 that can be used to provide wide-field images

608, a second module to provide narrow-field images 616, and a third module to detect image data 624 of the eye 628 and correct for optical distortions.

In some embodiments, the first module 604 is a TSLO including a line-scanning laser ophthalmoscope and a tracking component. The TSLO can drive tracking mirrors 632 to track a reference feature 636 of the eye 628 and to control an imaging beam of the second module.

The second module can be a high-speed spectral domain optical coherence tomography (SD)OCT imager to provide for high-resolution cross-sectional images 616. In some embodiments, a dichroic mirror 660 is used to acquire the wide-field images 608 and high-resolution cross section images 616 simultaneously. In some embodiments, a beamsplitter 642 directs a portion of the imaging beam from the light source 640 to the eye and another portion of the beam to the reference arm 644. The imaging beam reflected from the reference arm 644 and the imaging beam reflected from the eye 628 is directed by beam splitter 649 to the detection device 648.

The third module can be an adaptive optics (AO) component to sense and correct for ocular aberrations. In some embodiments, the third module is an AO component that provides for AO correction through use of a Hartmann-Shack wavefront sensor 652 and a wavefront compensation device 656 such as a MEMS-based deformable mirror (Boston Micromachines Inc.). In some embodiments, a stimulus or therapeutic laser 664 is combined by a dichroic mirror 668 in a common optical path with the imaging beam of the second module.

Figure 7:
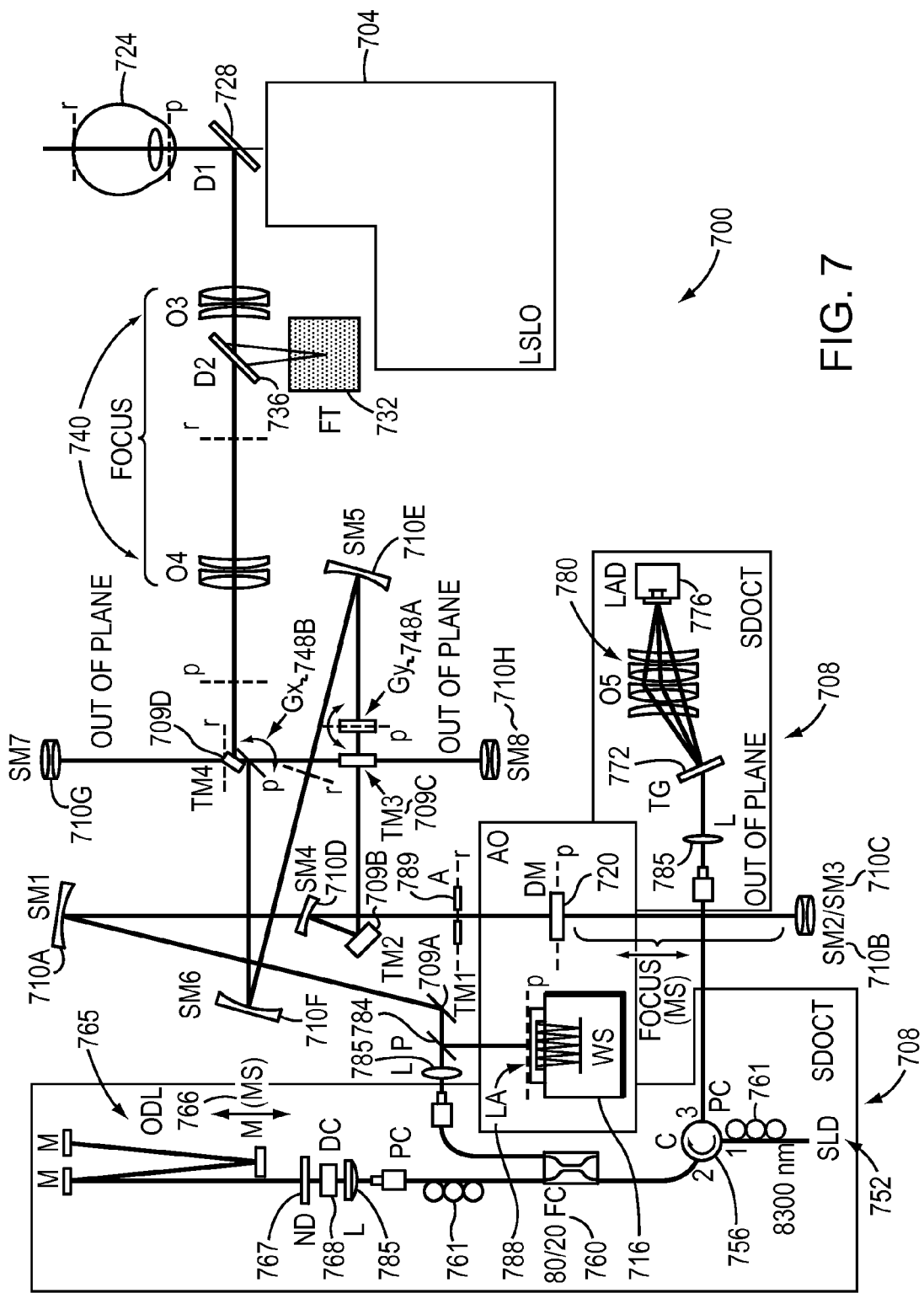
FIG. 7 is another schematic drawing of an illustrative embodiment of the apparatus.

FIG. 7 shows another illustrative embodiment of an imaging system 700. The first module is an LSLO component 704 that provides quasi-confocal en face fundus images over a wide field of view (up to about 30°) to allow for global orientation and localization of the OCT imager. The second module 708 is a SDOCT imager that can include the use of transverse scanning mirrors 709*a-d*, spherical focusing mirrors 710A-H, lenses 785, and a spectrometer. The third module 712 can provide AO correction through use of a Hartmann-Shack wavefront sensor 716 and a MEMS based deformable mirror 720 (DM, Boston Micromachines, Inc.). In some embodiments, the AO-SDOCT and LSLO beams are combined before entering the eye 724 with a dichroic mirror 728 in order to acquire and display the cross-sectional and en face images simultaneously.

The retinal imaging system can also include an integrated 8×8 LED array fixation target 732 and driver board controlled from the computer serial port. A portion of the beam reflected from the eye can be sent to the fixation target 732 by a beamsplitter 736. In some embodiments, a 60×60 cm breadboard contains the system optics and is situated above a rack-mount drawer that contains the driving electronics. In some embodiments, the entire housing (excluding the DM driver and computers) measures approximately 60 cm×60 cm×30 cm.

The LSLO module 704 can include a galvanometer-driven scanning mirror placed near the pupil conjugate. The wide-field image can be created by scanning a line created by the cylindrical lens through an objective lens and ophthalmoscopic lens onto the retina. Backscattered light originating at the retina is descanned and focused by another objective lens onto a 512 pixel linear array detector (Dalsa Inc.). This line-scanning approach creates quasiconfocal (1/z dependence of the confocal parameter) wide-field SLO retinal images. A split aperture can be used to block unwanted reflections that originate from both the cornea and the instrument optics. The LSLO optics can be designed to exhibit low chromatic aberrations over a 250 nm band (650-900 nm) and achieve nearly diffraction-limited performance across a wide 30° field.

The AO-SDOCT setup can combine a fiber-based interferometer and free-space optical front end that uses mirrors except for objective lenses 740 used for focus correction. In some embodiments, the use of mirrors elsewhere minimizes back reflections, chromatic distortion, and group velocity dispersion for SDOCT imaging. In some embodiments, each of the objectives is a commercially available achromat and a meniscus lens designed to minimize monochromatic and chromatic aberrations as well as to maintain field flatness. Defocus correction can be achieved by adjustment of the axial separation between this pair of objective lenses and/or translation of a motorized stage on which the deformable mirror 720 and a spherical mirror relay (SM2/SM3) 744A and 744B are affixed. The front objectives 740 can be used to achieve a larger range of focus correction (greater than about plus or minus 5 diopters (D)) useful in this compact, clinically relevant instrument. The computer controlled linear stage (Velmex Inc.) on which the DM 720 and SM2/SM3 710B-C are mounted can provide additional fine focus adjustment within the range of plus or minus 2 D. The deformable mirror 720 can necessitate these focusing components as its limited 4 μm stroke can only fully correct a subset of the potential patient population. While adjustment of the separation between front objectives changes retinal defocus in a manner that does not change the critical sample arm optical path length, it will change the axial location of the exit pupil. Conversely, adjustment of the DM stage changes path length, but not the pupil location. Therefore, in some embodiments, once the pupil of the patient is aligned and retina focused, the coarse objective focus is not adjusted throughout an imaging session. In some embodiments, the stage control software is configured so that the reference arm and focus stage (containing the pair SM2/SM3 and DM) are locked and small fine focus adjustments are automatically compensated with the reference arm stage to maintain matched path lengths in both arms of the SDOCT interferometer. The exit pupil of the LSLO imager can be aligned (both collinearly and parfocally) to the SDOCT exit pupil for ease of patient alignment.

In some embodiments, eight spherical focusing mirrors 710A-H relay four conjugate retinal and pupil planes to critical locations throughout the system. For correction of ocular aberrations in a double-pass configuration, the DM 720 and WS 716 can be placed at conjugate pupil planes. To utilizing transverse scanning with pupil centration, the horizontal and vertical scanning galvanometer mirrors (Gx, Gy) 748A and 748B can pivot about pupil conjugates. Utilization of spherical mirrors 710A-H in an off-axis arrangement can induce astigmatism that can reduce overall system performance as measured by the wavefront error or point spread function (PSF) of the beam input to the eye 724. To minimize this problem, in some embodiments, long focal length elements are used. In other embodiments, to counteract the aberrations while using shorter focal length optics, the spherical mirrors (SM5-SM8) 710E-H are grouped in matched pairs that are oriented in such a way that the angular beam deviation of one set is out of plane with respect to the other. The net effect of this arrangement is to cancel most of the astigmatism in the system, and any residual astigmatism can be eliminated with the off-axis reflection from SM1 710A. In some embodiments, the wavefront error induced by the optics over a maximum expected angular range of the OCT beam (plus or minus 5 degrees), including front lens relay, is $\lambda/10$ at 830 nm. Therefore, in some embodiments, very little DM stroke is allocated for correction of inherent system aberrations.

In some embodiments, the retinal system acquires OCT images by launching and collecting light in a fiber-based Michelson interferometer. Light from the OCT source 752 (e.g., a superluminescent diode) can be launched into a fiber circulator 756 and an 80/20 fiber coupler 760 to split signal between the sample and reference arms. Manual fiber polarization controllers 761 can be placed in each interferometer arm. In some embodiments, light directed to the eye 724 is reflected off spherical focusing mirrors 744A-H, galvanometer-driven transverse scanning mirrors 709A-D and the front dichroic beam splitter 728. The sample and reference arm paths can be matched with a free-space multipass optical delay line 765 with the final reflecting mirror mounted to a computer-controlled linear stage. In some embodiments, the reference arm includes a motorized stage 766, a neutral density filter 767 and a dispersion cube 768. A free-space delay line can minimize the dispersion mismatch between the reference and sample arms. The multipass design reduces the instrument footprint. In some embodiments, light backscattered from the eye 724 is combined at the coupler 760 with returned signal from the reference arm to generate fringes at the spectrometer. In some embodiments, the spectrometer arm of the SDOCT system uses a typical design including a transmission grating 772 (1200 p/mm, 830 μm λc, Wasatch Photonics Inc.) and 10 μm, 2048 pixel linear array detector (Atmel Inc.) 776. An objective lens 780 that includes of two meniscus lenses and two commercially available achromats focuses light onto the detector 776 can be used. In some embodiments, the SDOCT source 752 is a SLD centered at 830 nm with a spectral bandwidth of about 60 nm that achieves approximately 4 μm depth resolution in the eye as determined by the FWHM of the connecting cilia layer.

In a preferred embodiment, the third module includes a 92%/8% pellicle beam splitter 784 that extracts a portion of the imaging beam returning from the eye for wavefront sensing. In other embodiments, a separate beam with different wavelength for the AO beacon is used. The optical components can relay the pupil to the WS camera 788 placed at a conjugate plane with a factor of 1.3 magnification (nominal 7 mm pupil diameter is 9.0 mm at the camera). The Hartmann-Shack WS 716 can include a 65×65 element lenslet array with 0.4 mm pitch and 24 mm focal length (Adaptive Optics Associates Inc.). Reflections from the objective lens can be subtracted out of the WS image by acquiring a background image with no patient in the instrument with the relevant scan activated. In some embodiments, corneal reflections are reduced with placement of an aperture at a stationary retinal conjugate. Focal spots generated by the array can be detected with a 1024×1024 pixel, 12 mm CCD camera with a maximum frame rate of 60 Hz (Dalsa Inc.). In some embodiments, the wavefront compensator 720 includes a 141 element, 4.8 mm diameter, MEMS-based, continuous-surface, electrostatic-actuator-driven DM that has a maximum stroke of about 4 μm. Focal lengths of the spherical mirrors 710A-H can be chosen to demagnify a 7 mm pupil to 4.5 mm to underfill the clear aperture 789 of the deformable mirror 720. In some embodiments, the focal length of the fiber collimator input to the free-space portion of the SDOCT sample path is chosen to be 35 mm for an input beam diameter of approximately 8 mm that approximately fills the DM and matches the size of the 7 mm pupil at the WS. The limiting apertures in the system can be the galvanometer mirrors, which are sized just below the DM clear aperture 789.

Figure 8:
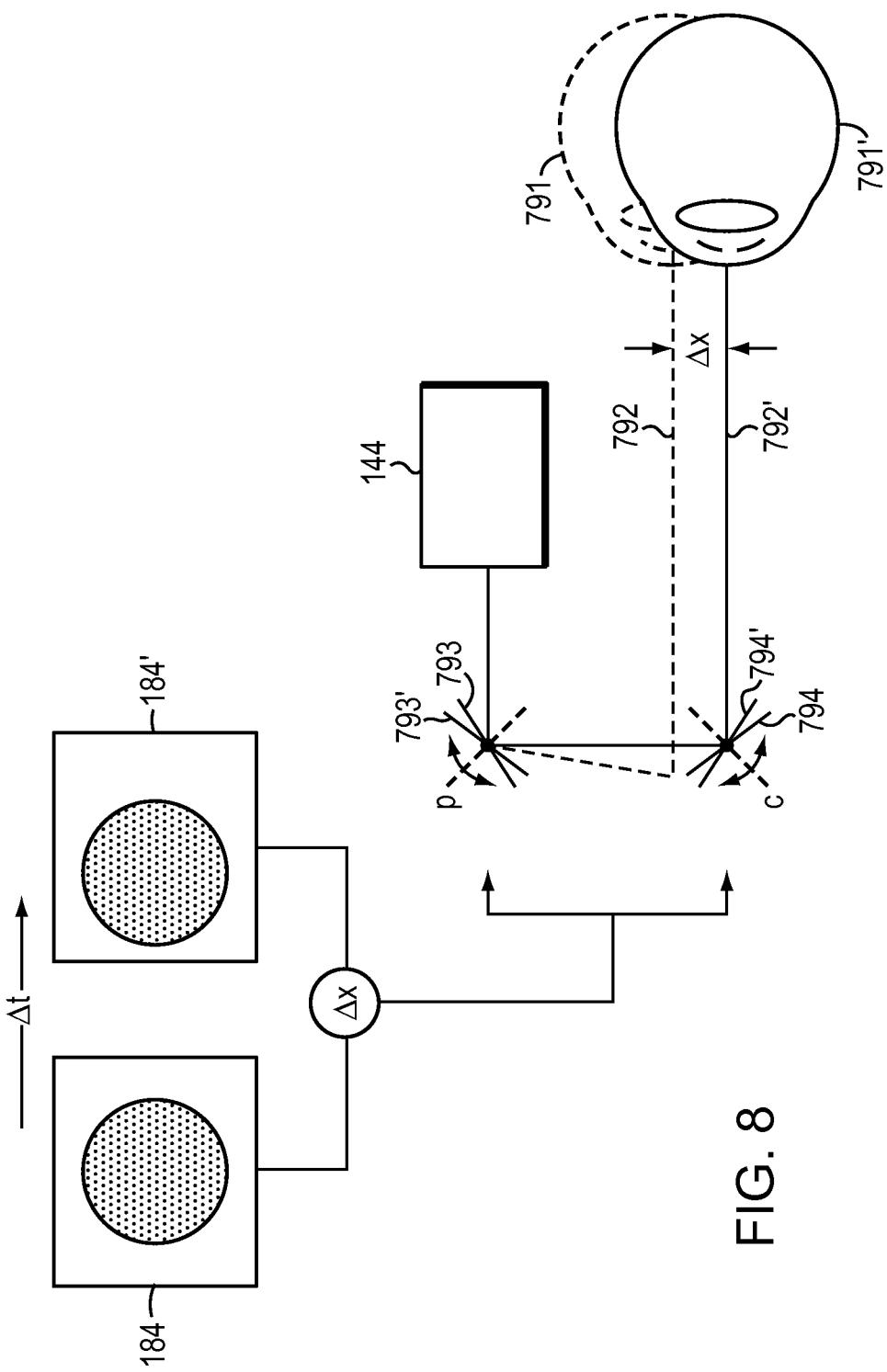
FIG. 8 is a schematic drawing showing a system for adjusting the imaging system for movement of the head.

FIG. 8 shows a system for adjusting the imaging system for movement of the head. Images from the wavefront sensor 176 can be used to track for translational and rotational motion of an eye. In some embodiments, the second module has a source 144 that generates the imaging beam. The host computer 163 can generate direction control signals to control the imaging beam of the second module to track relative to a reference feature 108. The host computer 163 can use the images 184 and 184' generated by the wavefront sensor 176 over a period of time (at) and apply a pupil/head tracker algorithm 185 to sense and calculate translational pupil and head position. For example, if the head moves, the wavefront map 184' appears shifted relative to wavefront map 184.

Image 184 corresponds to the location of the eye in a first position 791 while image 184' corresponds to the location of the eye in a second position 791'. Using the pupil/head tracker algorithm 185, the host computer 163 can generate translational direction control signals, rotational direction control signals about the pupil conjugate and rotational direction control signals about the center of the eye.

The translational control signals can be sent to the galvanometers 156 that adjust the scanning devices 156 according to pre-determined offset to adjust for the motion of the head. In some embodiments, the translational control signals allow the galvanometers 156 to move the imaging beam of from a first position 792 to a second position 792' in order to track the imaging beam relative to a reference feature as the eye and head move from the first position 791 to a second position 791'. For example, if the eye and head move by a translational distance $\Delta x$, the translational control signals control the galvanometers 156 move the imaging beam by a translational distance of $\Delta x$. FIG. 8 depicts the translational motion along one axis (e.g., the x-axis), although the same or a similar system can be used for a second axis (e.g., the y-axis).

Rotational control signals about the pupil conjugate 793 and/or the conjugate about the center of the eye 794 can be sent to the slave galvanometers 164. The rotational control signals can adjust the galvanometer in the pupil conjugate from a first position 793 to a second position 793' to track the imaging beam relative to a reference feature as the eye and head moves from a first position 791 to a second position 791'. The rotational control signals can also adjust the galvanometer in the conjugate about the center of the eye from a first position 794 to a second position 794' to track the imaging beam relative to a reference feature as the eye and head moves from a first position 791 to a second position 791'. This provides the ability to walk or translate the beam without rotation by adjustment of the mirrors at both conjugates for each axis simultaneously in a coordinated fashion. Compensating for translational movement of the head can be performed in an SLO embodiment or a OCT embodiment.

In some embodiments, the imaging system can re-lock after a subject blinks. For some very fast blinks, the system remains locked through the blink since any system bias is removed in the software. Thus, the tracker beam tends not to drift from its current position when presented with a uniform field absent a tracking target. However, for longer duration blinks, the tracker can lose lock when the eyelid passes across the tracked point. A re-lock algorithm can rapidly and automatically re-position the track beam to the previously tracked position. For example, the algorithm automatically determines the occurrence of loss of lock when the reflectance signal passes out of a region determined by upper and lower thresholds. When loss of lock occurs, the algorithm re-positions the tracker beam to the last locked position. As long as the subject does not shift their gaze by a large amount during the blink, the system re-acquires the target as soon as the subject opens their eyes after the blink. Compensating for blinking can be performed in an SLO embodiment or a OCT embodiment.

Exemplary stabilized retinal imaging systems with adaptive optics are described in Ferguson et al., "Tracking adaptive optics scanning laser ophthalmoscope," Proc. of SPIE Vol. 6138, 613810, (2006); Ferguson et al., "Adaptive optics scanning laser ophthalmoscope for stabilized retinal imaging," OPTICS EXPRESS 3354, Vol. 14, No. 8 (2006); Hammer et al., "Precision targeting with a tracking adaptive optics scanning laser ophthalmoscope," Proc. of SPIE Vol. 6138, 613811, (2006); Hammer et al., "High resolution retinal imaging with a compact adaptive optics spectral domain optical coherence tomography system," Proc. of SPIE Vol. 6426 (2007); and Bigelow et al., "Compact multimodal adaptive-optics spectral-domain optical coherence tomography instrument for retinal imaging," J. Opt. Soc. Am. A 24:1327 (2007); the disclosures of which are herein incorporated by reference in their entireties.

While the invention has been particularly shown and described with reference to specific illustrative embodiments, it should be understood that various changes in form and detail may be made without departing from the spirit and scope of the invention.

What is claimed:

1. An apparatus for imaging a retina of an eye, comprising:
    a first module to track a reference feature of the retina of the eye;
    an second module comprising:
        a source for an imaging beam;
        a scanning device to move the imaging beam along a portion of the retina of the eye; and
        a first detection device to receive a signal associated with an image of the portion of the retina scanned, the first module controlling the position of the imaging beam relative to the reference feature to correct for motion of the eye; and
    a third module comprising:
        a wavefront sensor to detect an optical distortion; and
        a wavefront compensator to correct for the optical distortion in the imaging beam scanned on the retina of the eye.

2. The apparatus of claim 1 further comprising a controller in communication with the first module, the second module, and the third module; and the scanning device of the second module including a first galvanometer and a second galvanometer, the controller delivering a first direction control signal to the first galvanometer and a second direction control signal to the second galvanometer to control a translational position of the imaging beam to track relative to the reference feature.

3. The apparatus of claim 2 wherein the controller receives, from the wavefront sensor of the third module, information relating to translational position of the eye to generate the first direction control and the second direction control.

4. The apparatus of claim 1 further comprising a stimulus beam in a common optical path with the imaging beam of the second module for vision studies.

5. The apparatus of claim 1 further comprising at least one pair of spherical mirrors to minimize astigmatism of the imaging beam.

6. The apparatus of claim 1 wherein the first module comprises a line scanning laser ophthalmoscope to provide a wide-field optical image.

7. The apparatus of claim 1 wherein the second module comprises a confocal flying spot scanning laser ophthalmoscope to provide a narrow-field optical image.

8. The apparatus of claim 1 wherein the second module comprises a spectral domain optical coherence tomography to provide a narrow-field optical image.

9. The apparatus of claim 1 wherein the source for the imaging beam is a superluminescent diode.

10. The apparatus of claim 1 wherein at least one scanner is positioned at a center-of-rotation conjugate of the eye to substantially simultaneously track a pupil and the retina of the eye.

11. The apparatus of claim 1 wherein a first scanner is positioned a pupil conjugate and a second scanner is positioned at a center-of-rotation conjugate to translate the imaging beam.

12. The apparatus of claim 1 wherein the wavefront sensor of the third module receives a first portion of the imaging beam of the second module reflected from the retina of the eye and detects the distortion of the retina of the eye.

13. The apparatus of claim 1 wherein the wavefront compensator is an adaptive optical element.

14. The apparatus of claim 13 wherein the adaptive optical element comprises a deformable mirror.

15. The apparatus of claim 1 wherein the second module further comprises at least one spherical mirror to compensate for distortions in the retina of the eye.

16. A method for imaging a retina of an eye, comprising:
    tracking a reference feature of the retina of the eye;
    scanning an imaging beam along a portion of the retina;
    controlling the position of the imaging beam relative to the reference feature to correct for motion of the eye;
    detecting, by a wavefront sensor, a signal associated with an image of the portion of the retina scanned; and
    compensating for an optical distortion of the image of the retina by correcting the imaging beam scanned on the retina.

17. The method of claim 16 further comprising:
    identifying a target feature in the image of the portion of the retina scanned; and
    delivering a therapeutic beam to the target feature to treat the eye.

* * * * *